United States Patent [19]

Nickoloff et al.

[11] Patent Number: 5,707,624
[45] Date of Patent: Jan. 13, 1998

[54] TREATMENT OF KAPOSI'S SARCOMA BY INHIBITION OF SCATTER FACTOR

[75] Inventors: Brian J. Nickoloff, Dexter, Mich.; Yahti M. Naidu, San Diego, Calif.; Eliot M. Rosen, Port Washington, N.Y.; Peter J. Polverini, Ann Arbor, Mich.

[73] Assignee: The Regents of the University of Michigan, Ann Arbor, Mich.

[21] Appl. No.: 253,728

[22] Filed: Jun. 3, 1994

[51] Int. Cl.$^6$ .................................................. A61K 39/395
[52] U.S. Cl. .................... 424/158.1; 424/145.1; 424/143.1; 424/152.1
[58] Field of Search .......................... 424/145.1, 152.1, 424/143.1, 158.1; 435/7.23; 436/63, 64, 813

[56] References Cited

PUBLICATIONS

Corallini, et al., *Cancer Research*, vol. 53, No. 22, pp. 5569–5575, 1993.
Adams, J.C. et al. "Production of Scatter Factor by NDK, a Strain of Epithelial Cells, and Inhibition of Scatter Factor Activity by Suramin," *J. Cell Sci.* 98:385–394 (1991).
Angerer, L.M. et al. "Demonstration of Tissue–specific Gene Expression by In Situ Hybridization," *Meth. Enzymol.* 152:649–660 (1987).
Bacchetti, P. et al., "Concise Communications," *J. Infect. Dis.* 157:1044–1047 (1988).
Bhargava, M. et al., "Scatter Factor and Hepatocyte Growth Factor: Activities, Properties, and Mechanism," *Cell Growth & Diff.* 3:11–20 (1992).
Bottaro, D.P. et al., "Identification of the Hepatocyte Growth Factor Receptor as the c–met Proto–Oncogene Product," *Science* 251:802–804 (1991).
Chou, Q. et al., "Prevention of Pre–PCR Mis–Priming and Primer Dimerization Improves Low–Copy–Number Amplifications," *Nucleic Acids Res.* 20:1717–1723 (1992).
Clerici, M. et al., "$AT^H1 \rightarrow T_H2$ Switch is a Critical Step in the Etiology of HIV Infection," *Immunol. Tod.* 14:107–111 (1993).
Damle, N.K. et al., "Proliferation of Human T Lymphocytes Induced with Superantigens is not Dependent on Costimulation by the CD28 Counter–Receptor B7," *J. Immunol.* 150:726–735 (1993).
R.F., "Kaposi's Sarcoma Revisited," *Hum. Pathol.* 15:1013–1017 (1984).
Ensoli, B. et al., "AIDS–Associated Kaposi's Sarcoma: A Molecular Model for its Pathogenesis," *Cancer Cells* 1:93–96 (1989).
Ensoli, B. et al., "AIDS–Kaposi's Sarcoma–Derived Cells Express Cytokines with Autocrine and Paracrine Growth Effects," *Science* 243:223–226 (1989).
Ensoli, B. et al., "Tat Protein of HIV–1 Stimulates Growth of Cells Derived from Kaposi's Sarcoma Lesions of AIDS Patients," *Nature* 345:84–86 (1990).
Errante, D. et al., "Management of AIDS and its Neoplastic Complications," *Eur. J. Cancer* 27:380–389 (1991).

Feinberg, A.P. et al., "A Technique for Radiolabeling DNA Restriction Endonuclease Fragments to High Specific Activity," *Anal. Biochem.* 132:6–13 (1983).
Folkman, J., "Angiogenesis in Psoriasis: Therapeutic Implications," *J. Invest. Dermatol.* 59:40–43 (1972).
Gill, P.S. et al., "Advanced Acquired Immune Deficiency Syndrome–Related Kaposi's Sarcoma," *Cancer* 65:1074–1080 (1990).
Good, D.J., "A Tumor Suppressor–Dependent Inhibitor of Angiogenesis is Immunologically and Functionally Indistinguishable form a Fragment of Thrombospondin," *PNAS (USA)* 87:6624–6628 (1990).
Grant, D.S. et al., "Scatter Factor Induces Blood Vessel Formation In Vivo," *PNAS (USA)* 90:1937–1941 (1993).
Henriksson, P. et al., "Identification of Intracellular Factor XIII in Human Monocytes and Macrophages," *J. Clin. Invest.* 76:528–534 (1985).
Huang, Y. et al., "Cultured Kaposi's Sarcoma Cell Lines Express Factor XIIIa, CD14, and VCAM–1, but Not Factor VIII or ELAM–1," *Arch. Dermatol.* 129:1291–1296 (1993).
Huang, Y.Q. et al., "HPV–16–Related DNA Sequences in Kaposi's Sarcoma," *Lancet* 399:515–518 (1992).
Karasek, M.A. *In Dermal Immune System* Nickoloff, B.J. ed CRC Press, Boca Ratan, pp. 149–162 (1992).
Kinoshita, T, et al., "Marked Increase of HGF mRNA in Non–Parenchymal Liver Cells of Rats Treated with Hepatotoxins," *Biochem. Biophys. Res. Commun.* 165:1229–1234 (1989).
Kupchik, H.Z. et al., "Immunochemical Studies of Carcinoembryonic Antigens: Methodologic Considerations and Some Clinical Implications," *J. Natl. Cancer Inst.* 52:413–423 (1974).
Lemp, G.F. et al., "Survival Trends for Patients with AIDS," *JAMA* 263:402–406 (1990).
Lipton, B.H. et al., "Histamine–Modulated Transdifferentiation of Dermal Microvascular Endothelial Cells," *Exp. Cell Res.* 199:279–291 (1992).
Matsumoto, K. et al., "Identification and Characterization of Injurin, and Inducer of Expression of the Gene for Hepatocyte Growth Factor," *PNAS (USA)* 89:3800–3804 (1992).

(List continued on next page.)

*Primary Examiner*—Toni R. Scheiner
*Attorney, Agent, or Firm*—Harness, Dickey & Pierce, P.L.C.

[57] ABSTRACT

Methods of treating Kaposi's sarcoma (KS) by inhibiting the effect of scatter factor (SF), also known as hepatocyte growth factor (HGF), are provided. The methods of the present invention include antibody therapy wherein an antibody to SF is introduced into a patient to decrease active SF levels thereby decreasing the incidence of new tumors as well as leading to regression of established tumors by blocking SF-mediated tumor cell proliferation and neovascularization. The present invention further provides methods of inhibiting the effects of SF by introducing into a patient means for inhibiting binding of SF to the SF receptor, the c-met proto-oncogen. Means for inhibiting SF binding to the receptor include introducing into a patient an antibody to the c-met receptor or introducing a non-stimulatory ligand that will bind and thereby inhibit the receptor.

18 Claims, 9 Drawing Sheets

OTHER PUBLICATIONS

Meyaard, L. et al., "T–Cell Dysfunction in HIV Infection: Anergy Due to Defective Antigen–Presenting Cell Function?" *Immunol. Tod.* 14:161–164 (1993).

Miles, S.A. et al., "Oncostatin M as a Potent Mitogen for AIDS–Kaposi's Sarcoma–Derived Cells," *Science* 255:1432–1434 (1992).

Miles, S.A. et al., "AIDS Kaposi Sarcoma–Derived Cells Produce and Respond to Interleukin 6," *PNAS (USA)* 87:4068–4072 (1990).

Mitsuyasu, R.T., "AIDS–Related Kaposi's Sarcoma: A Review of its Pathogenesis and Treatment," *Blood Rev.* 2:222–231 (1988).

Miyazawa, K. et al., "Molecular Cloning and Sequence Analysis of cDNA for Human Hepatocyte Growth Factor," *Biochem. Biophys. Res. Commun.* 163:967–973 (1989).

Montagnier, L. et al., "Factors and Mechanisms of AIDS Pathogenesis," *Science Challenging AIDS* (Proceedings Based on the VIIth International Conference of AIDS), pp. 51–70 (1991).

Nakamura, T. et al., "Molecular Cloning and Expression of Human Hepatocyte Growth Factor," *Nature (London)* 342:440–443 (1989).

Nakamura, S. et al., "Kaposi's Sarcoma Cells: Long–Term Culture with Growth Factor from Retrovirus–Infected CD4+ cells," *Science* 242:426–430 (1988).

Nickoloff, B.J. et al., "Factor XIIIa–Expressing Dermal Dendrocytes in AIDS–Associated Cutaneous Kaposi's Sarcomas," *Science* 243:1736–1737 (1989).

Nickoloff, B.J. et al., "Preferential Binding of Monocytes–and Leu 2+T Lymphocytes to Interferon–Gamma Treated Culture Skin Endothelial Cells and Keratinocytes," *Arch. Dermatol. Res.* 280:235–245 (1988).

Nickoloff, B.J., "The Human Progenitor Cell Antigen (CD34) is Localized on Endothelial Cells, Dermal Dendritic Cells, and Perifollicular Cells in Formalin–Fixed Normal Skin, and on Proliferating Endothelial Cells and Stromal Spindle–Shaped Cells in Kaposi's Sarcoma," *Arch. Dermatol.* 127:523–529 (1991).

Nickoloff, B.J, et al., "Immunohistochemical Detection of Papillomavirus Antigens in Kaposi's Sarcoma," *Lancet* 339:548–549 (1992).

Nickoloff, B.J., "PECAM–1 (CD31)is Expressed on Proliferating Endothelial Cells, Stromal Spindle–Shaped Cells, and Dermal Dendrocytes in Kaposi's Sarcoma," *Arch. Dermatol.* 129:250–251 (1993).

Nickoloff, B.J. et al., "The Spindle–Shaped Cells in Cutaneous Kaposi's Sarcoma, Histologic Simulators Include Factor XIIIa Dermal Dendrocytes," *Am. J. Pathol.* 135:793–800 (1989).

O'Connell, K.A. et al., "Cloned Spindle and Epithelioid Cells from Murine Kaposi's Sarcoma–Like Tumors are of Endothelial Origin," *J. Invest. Dermatol.* 100:742–745 (1993).

O'Connell, K.A. et al., "Endothelial Cells Transformed by SV40 T Antigen Cause Kaposi's Sarcomalike Tumors in Nude Mice," *Am. J. Pathol.* 139:743–749 (1991).

O'Connell, K.A., et al. "A mouse Lymphold Endothelial Cell Line Immortalized by Simian Virus 40 Binds Lymphocytes and Retains Functional Characteristics of Normal Endothelial Cells," *J. Immunol.* 144:521–525 (1990).

Pantaleo, G. et al., "The Immunopathogenesis of Human Immunodeficiency Virus Infection," *N. Eng. J. Med.* 328:327–335 (1993).

Payne, S.F. et al., "Survival Following Diagnosis of Kaposi's Sarcoma for AIDS Patients in San Francisco," *J. Acquir. Immun. Def. Syndr.* 3 Suppl. 1:S14–S17 (1990).

Penn, I., "Neoplastic Consequences of Transplantation and Chemotherapy," *Can. Detect. Prev.* (suppl) 1:149–157 (1987).

Polverini, P.J. et al., "Induction of Neovascularization In Vivo and Endothelial Proliferation In Vitro by Tumor–Associated Macrophages," *Lab. Invest.* 51:635–642 (1984).

Rabkin, C.S. et al., "Kaposi's Sarcoma in Three HIV–1–Infected Cohorts," *J. Acq. Imm. Def. Synd* 3(suppl):S38–S43 (1990).

Rastinejad, F., "Regulation of the Activity of a New Inhibitor of Angiogenesis by a Cancer Suppressor Gene," *Cell* 56:345–348 (1989).

Rong, S. et al., "Tumorigenicity of the met Proto–Oncogene and the Gene for Hepatocyte Growth Factor," *Mol. Cell Biol.* 12:5152–5158 (1992).

Rosen, E.M. et al., "Scatter Factor Stimulates Migration of Vascular Endotheliumand Capillary–Like Tube Formation," *Cell Motility Factors*, ed. by. Goldberg, I.D., Birkhouser–Verlag, Basel/Switzerland, pp. 76–88 (1991).

Rosen, E.M. et al., "Purified Scatter Factor Stimulates Epithelial and Vascular Endothelial Cell Migration," *Proc. Soc. Exp. Biol. Med.* 195:34–43 (1990).

Rosen, E.M. et al., "Scatter Factor Regulates Vascular Endothelial Cell Motility," *Cancer Invest.* 8:647–650 (1990).

Rothman, S., "Some Clinical Aspects of Kaposi's Sarcoma in the European and North American Population," *Acta. Int. Cancer* 18:364–371 (1962).

Salahuddin, S.Z. et al., "Angiogenic Properties of Kaposi's Sarcoma–Derived Cells After Long–Term Culture In Vitro," *Science* 242:430–433 (1988).

Sambrook, J. et al., "Molecular Cloning: A Laboratory Manual" 2nd ed. Cold Springs Harbor Laboratory, NY, pp 9.31–9.57 (1989).

Savage, C.O. et al., "Endothelial Cell Lymphocyte Function–Associated Antigen–3 and an Unidentified Ligand Act in Concert to Provide Costimulation to Human Peripheral Blood CD4+T Cells," *Cell Immunol.* 137:150–163 (1991).

Sheppard, H.W. et al., "AIDS and Programmed Cell Death," *Immunol. Tod.* 12:423 (1991).

Stoker, M. et al., "Scatter Factor is a Fibroblast–Derived Modulator of Epithelial Cell Mobility," *Nature (London)* 327:239–242 (1987).

Weich, H.A., et al., "AIDS–Associated Kaposi's Sarcoma–Derived Cells in Long–Term Culture Express and Synthesize Smooth Muscle Apha–Actin," *Am. J. Pathol.* 139:1251–1258 (1991).

Weidner, K.M. et al., "Evidence for the Identity of Human Scatter Factor and Human Hepatocyte Growth Factor," *PNAS (USA)* 88:7001–7005 (1991).

Weiss, R.A., "How Does HIV Cause AIDS?" *Science* 260:1273–1279 (1993).

Yang, X.M. et al., "Expression of the met/Hepatocyte Growth Factor/Scatter Factor Receptor and Its Ligand during Differentiation of Murine P19 Embryohal Carcinoma Cells," *Dev. Biol.* 157:308–320 (1993).

Yarchoan, R. et al., "Treatment of Acquired Immunodeficiency Syndrome," *Can. Chemother. Biol. Respon. Modif.* 11:379–415 (1990).

Zisbrod, Z. et al., "Kaposi's Sarcoma After Kidney transplantation Report of Complete Remission of Cutaneous and Visceral Involvement," *Transplantation* 30:383–384 (1980).

TREATMENT OF KAPOSI'S SARCOMA BY INHIBITION OF SCATTER FACTOR

SPONSORSHIP

Work on this invention was supported in part by United States Public Health Service grants HL 39926 (PJP), AR40065, AR01823 and AR40488 (BJN). The government has certain rights in the invention.

FIELD OF THE INVENTION

The present invention relates generally to a method of treating Kaposi's sarcoma and more particularly, to a method of treating Kaposi's sarcoma by inhibiting the effect of scatter factor, also known as hepatocyte growth factor.

BACKGROUND OF THE INVENTION

Kaposi's sarcoma (KS), a complex multicellular neoplasm, is one of the most common sequela of acquired immunodeficiency syndrome (AIDS). It was first described in 1872 as a rare malignancy characterized by multiple skin nodules on the lower extremities of elderly men of Mediterranean and Southern European extraction. Kaposi's sarcoma can also metastasize to extracutaneous sites such as the liver and viscera. KS gained tremendous notoriety when its incidence dramatically increased in association with AIDS as a result of HIV-1 infection. In fact, approximately one-third of all patients with HIV-1 infection will develop KS.

In addition to HIV-1-related KS, there are other epidemiological forms, many of which share frequent association with either neoplasms or immune system dysfunction. One form of KS tumor referred to as the "classical" form develops in elderly men typically with lymphoreticular neoplasms, and is a relatively low grade malignancy (Rothman, S., Acta. Int. Cancer 18:364–371 (1962)). Another form referred to as the "acquired" form can be seen in organ transplant patients or in individuals treated with immunosuppressive therapy (Zibrob, Z. et al., Transplantation 30:383–384 (1980) and Penn, I, Can. Detect. Prev. (suppl) 1:149–157 (1987)). KS that develops in patients with AIDS is called the "epidemic" or HIV-related form. This form is the most clinically aggressive with approximately 20% of patients suffering significant morbidity from their KS lesions and an increasing proportion dying from complications due to KS. Lemp, G. F. et al, JAMA 263:402–446 (1990); Gill, P. S. et al., Cancer 65:1074–1108 (1990); Bacchetti, P. et al., J. Infect. Dis. 157:1040–1047 (1988); Rabkin, C. S. et al., J. Acq. Imm. Del. Synd 3(suppl) :538–543 (1990) and Errante, D. et al., Eur. J. Cancer 27:380–389 (1991)).

Etiological agents of the epidemic form of KS other than HIV-1 such as the possible role of an environmental, genetic or infectious cofactor, have been suggested. In addition, the unusual prevalence of KS in sexually acquired AIDS has prompted speculation regarding the possible role of an infectious cofactor such as human papillomavirus (HPV) (Huang, Y. Q. et al., Lancet 399:515–518 (1992); Nickoloff, B. J, et al., Lancet 339:548–549 (1992)) (Huang, Y. Q. et al., Lancet. 399:515–518 (1992) and Nickoloff, B. J. et al., Lancet339:548–549 (1992)). However, there remains a lack of knowledge regarding possible causative agents.

A principal obstacle in developing a treatment for KS has been the lack of knowledge regarding the etiology and the pathophysiology of KS. KS is characterized both by tumor cell growth and neovascularization. KS lesions contain multiple cellular constituents, including proliferating endothelial cells, an expanded population of dermal dendrocytes that express factor XIIIa (a transglutaminase), lymphocytes, and a population of spindle-shaped tumor cells. The relationship between these cellular constituents has not been clearly delineated. It has been hypothesized that KS tumor cells are derived from endothelial cells (Dorfman, R. F., Hum. Pathol. 15:1013–1017 (1984)), dermal dendrocytes (Nickoloff, B. J. et al., Am. J. Pathol. 135:793–800 (1989)), and smooth muscle cells (Weich, H. A., et al., Am. J. Pathol. 139–1251–1258 (1991)). Endothelium, dendrocytes, and KS tumor cells in vivo share a number of immunophenotypic features, including expression of CD34 (human progenitor cell antigen), vascular cell adhesion molecule-1 (VCAM-1), and CD31 (platelet endothelial cell adhesion molecule-1) (Nickoloff, B. J., Arch. Dermatol. 127:523–529 (1991) and Nickoloff, B. J., Arch Dermatol. 129:250–251 (1993)).

The biological activity of conditioned medium obtained from KS cells includes angiogenic factors and cytokines such as IL-1$\beta$, GM-CSF, TGF-$\beta$, and bFGF. (Ensoli, B. et al., Cancer Cells 1:93–96 (1989); Nakamura, S. et al., Science 242:430–433 (1988) and Ensoli, B. et al., Science 243:223–226 (1989)) Much interest has been generated among researchers in elucidating the nature of the factor, or cofactors, that are produced by the retroviral infected T-cells, responsible for mediating KS tumor cell growth. Accepted molecular candidates for KS tumor cell mitogens include: oncostatin M (Miles, S. A. et al., Science 255:1432–1434 (1992)), IL-6 (Miles, S. A. et al., PNAS 87:4068–4072 (1990) and Miles, S. A. et al., Int. Conf. AIDS 7:55–58 (1991)), and the HIV-1 tat protein (Ensoli, B. et al., Nature 345:84–86 (1990)).

Current treatment modalities for KS including nonspecific treatments such as cryotherapy, surgery and administration of interferons, have not been successful in prolonging survival of patients suffering from KS. In addition, despite an overall improvement in survival trends for all HIV-1 infected patients, it has been reported that the survival trend for those HIV-1 infected individuals with KS has actually decreased. Payne, S. F. et al., J. Acquir. Imm. Defic. Syndr. 3 Suppl. 1:S14–S17 (1990). This lack of clinical improvement in terms of survival can be directly attributed to the absence of improved therapies for KS, while the other complications of HIV-1 have been more adequately dealt with. It is thus clear that new therapeutic methods for treating KS are needed.

It would thus be desirable to provide a method for treating KS. It would also be desirable to provide a method for inhibiting the growth and progression of KS cells. It would further be desirable to provide a method for inhibiting the growth and progression of KS tumors by blocking or inhibiting the expression of a cytokine important in the growth and progression of KS cells.

SUMMARY OF THE INVENTION

Methods of treating Kaposi's sarcoma (KS) by inhibiting the effect of scatter factor (SF), also known as hepatocyte growth factor (HGF), are provided. The present invention shows that SF, a cytokine produced by mesenchymal cells, participates in the initiation and maintenance of KS lesions and thus plays a pathophysiologically relevant role in KS lesions. Endothelial cell proliferation and neovascularization are common features of the KS lesion. SF has also been identified within KS lesions and SF mRNA has been found in KS cells. It is shown that SF induces endothelial cells to become spindle-shaped, express the dermal dendrocyte/KS tumor cell marker factor XIIIa and have a ctyokine profile similar to that of KS cells. It is shown that SF has growth-promoting activity for KS tumor cells as well as potent pro-angiogenic activity. In addition, it has now been shown that the introduction of an antibody to SF decreases KS tumor cell proliferation and pro-angiogenic activity.

The present invention thus provides methods of treating KS by inhibiting the effects of SF. The methods of the present invention include antibody therapy wherein an antibody to SF is introduced into a patient to decrease active SF levels thereby decreasing the incidence of new tumors as well as leading to regression of established tumors by blocking SF-mediated tumor cell proliferation and neovascularization. The methods of the present invention also include decreasing SF levels by suppressing the production of SF or accessory cytokines involved in the induction of SF production, for example by introducing antisense constructs into KS-associated host cell populations such as macrophages, which are a rich source of SF. The present invention further provides methods of inhibiting the effects of SF by introducing into a patient means for inhibiting binding of SF to the SF receptor, the c-met proto-oncogen. Means for inhibiting SF binding to the receptor include introducing into a patient an antibody to the c-met receptor or introducing a non-stimulatory ligand that will bind and thereby inhibit the receptor.

The present invention also provides methods of treating KS by introducing into a patient means of inhibiting at least one of a group of KS mitogens such as oncostatin M and IL-6, in addition to inhibiting the effects of KS, for example by decreasing SF levels or active SF levels, and/or by inhibiting SF binding to the c-met receptor. In addition, the methods of the present invention include treating KS by employing conventional therapies such as chemotherapy in combination with inhibiting the effects of SF as described herein.

BRIEF DESCRIPTION OF THE DRAWINGS

The various advantages of the present invention will become apparent to one skilled in the art by reading the following specification and subjoined claims and by referencing the following drawings in which:

FIG. 6 is a graph showing the response of KS cells to various growth factors.

DETAILED DESCRIPTION OF THE PREFERRED EMBODIMENTS

Figure 1A:
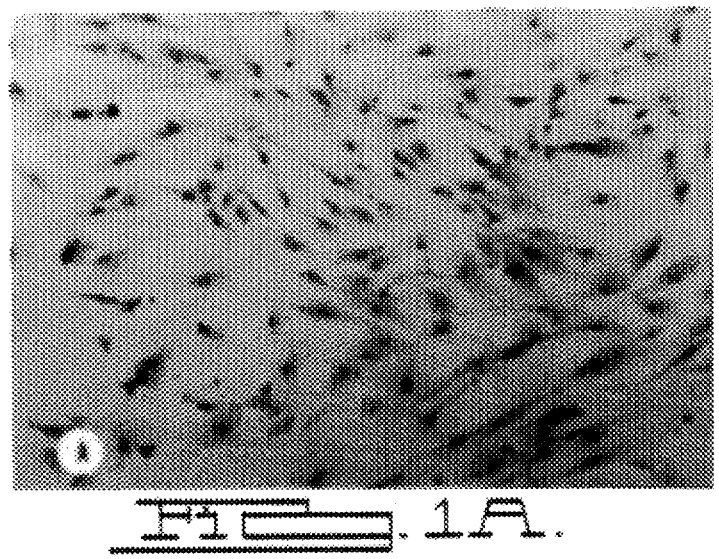
FIG. 1, photos A-F, are photographs showing the conversion of human endothelium to a KS tumor cell-like phenotype.
Figure 1B:
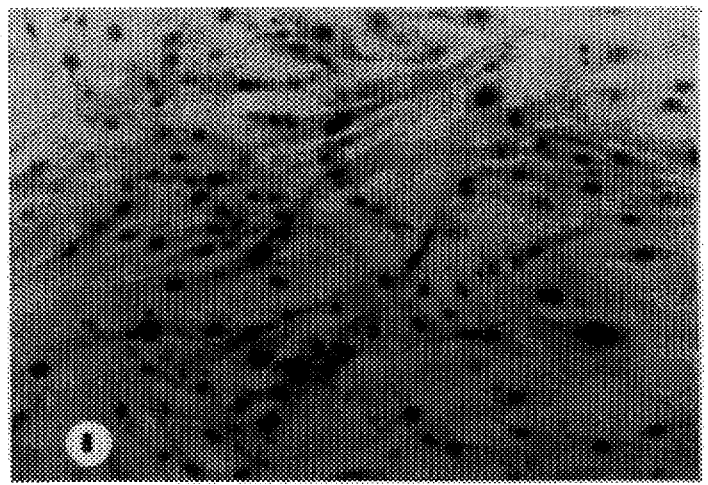
Figure 1C:
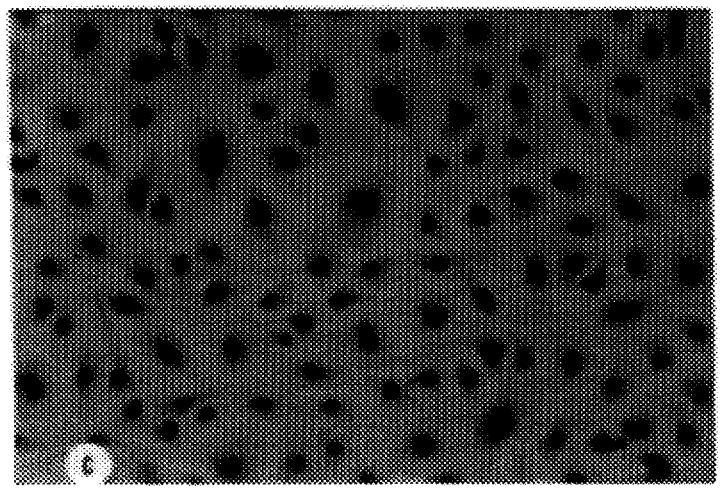
Figure 1D:
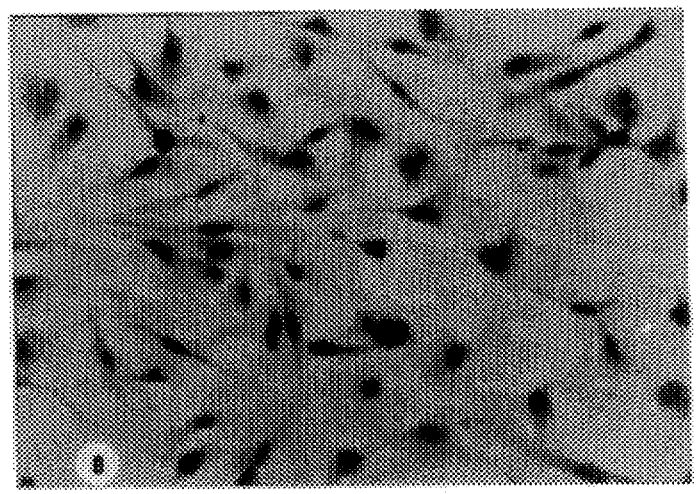
Figure 1E:
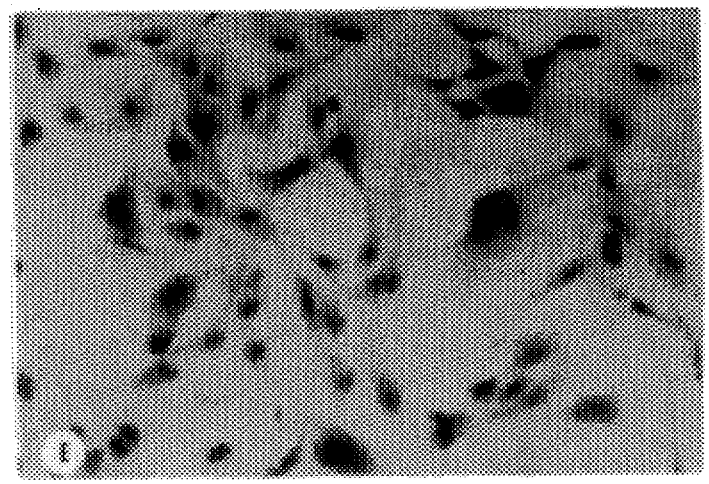
Figure 1F:
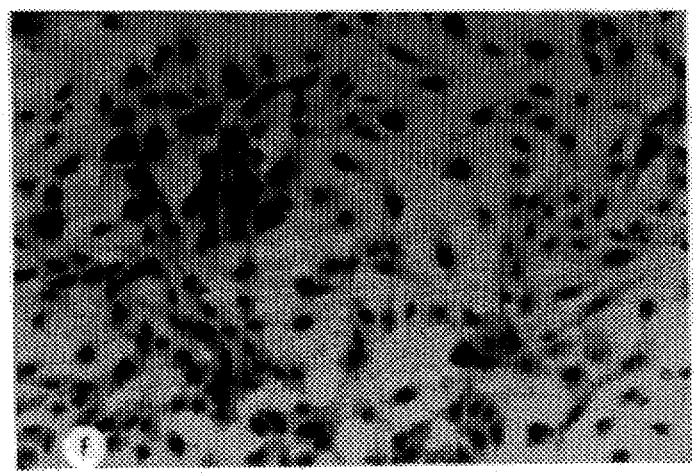

Methods of treating Kaposi's sarcoma (KS) by inhibiting or preventing KS cell growth are provided herein. The methods of the present invention inhibit the effect of scatter factor (SF), a cytokine produced by mesenchymal cells, which is shown to induce endothelial cells to become spindle-shaped, express dermal dendrocyte/KS tumor cell marker factor XIIIa and have a cytokine profile similar to that of KS cells, including induction of IL-1β, IL-6 and IL-8 mRNA. SF has growth-promoting activity for KS tumor cells as well as pro-angiogenic activity. The methods of the present invention include decreasing SF levels by antibody therapy, wherein an antibody to SF is introduced into a patient. SF levels may also be decreased by suppressing the production of SF or accessory cytokines involved in the induction of SF production, by introducing antisense constructs into KS-associated cell populations. The methods of the present invention also include inhibiting the KS tumor cell growth-promoting effects and pro-angiogenic activity effects of SF by blocking the receptor to SF, the c-met proto-oncogen, and therefore inhibiting SF binding. The c-met receptor may be blocked by introducing into a patient an antibody to the receptor or, by introducing a non-stimulatory ligand capable of binding but not stimulating the receptor. The methods of the present invention also include treating KS by introducing into a patient a means of inhibiting at least one of a group of KS mitogens such as the cytokines oncostatin M and IL-6, in combination with inhibiting the effects of SF. In addition, the methods of the present invention include treating KS by employing conventional therapies such as chemotherapy in combination with inhibiting the effects of SF as described herein.

SF was originally characterized as a fibroblast-derived cytokine that caused normally cohesive epithelial cell colonies to spread out and to separate into individual cell, i.e., to scatter. Stoker, M. et al., *Nature* (London) 327:238–242 (1987). SF was later found to be identical to hepatocyte growth factor (HGF) (Weidner, K. M. et al., *PNAS (USA)* 88:7001–7005 (1991) and Bhargava, M. et al., *Cell Growth & Diff.* 3:11–20 (1992)), a serum-derived mitogen (Nakamura, T. et al., *Nautre* (London) 342:440–443 (1989) and Miyazawa, K. et al., *Biochem. Biophys. Res. Commun.* 163:967–973 (1989)). SF is a heterodimeric glycoprotein composed of a 60 kDa alpha chain and a 30 kDa beta chain, and is similar to that of the blood coagulation proenzyme plasminogen (Nakamura, T. et al., *Nautre* (London) 342:440–443 (1989)). The receptor for SF, the c-met proto-oncogen is expressed by endothelial cells, dermal dendrocytes and KS spindle-shaped tumors.

It has recently become possible to propagate KS tumor cells in vitro by the use of KS cell growth medium (KSGM), a special medium that contains filtered, conditioned medium from HTLV-II infected human T lymphocytes (Nakamura, S. et al., *Science* 242:425–430 (1988) and Salahuddin, S. Z. et al., *Science* 242:430–433 (1988)). Studies of cultured KS cells have revealed that these cells express the dermal dendrocyte marker factor XIIIa, but do not express the endothelial cell markers factor VIII antigen or endothelial cell adhesion molecule-1 (ELAM-1)(Huang, Y. et al., *Arch. Dermatol.* 129:1291–1296 (1993)). The present invention shows that cultured, normal, human endothelial cells can be converted to a KS tumor cell-like phenotype by treatment with conditioned medium from HTLV-II infected T lymphocytes. The present invention further shows that the administration of antibodies to SF is effective in reducing proliferation of KS cells.

Although it is not the intent herein to be bound by any particular mechanism by which SF regulates the growth of KS cells, a model has been postulated and supported with experimental data. Specific Example 3 more fully describes the model, however briefly, it is believed that retroviral infection of T cells causes these cells to produce SF locally, which stimulates endothelial cells to migrate into adjacent perivascular sites. The SF stimulated endothelial cells undergo phenotypic conversion and accumulate within the perivascular interstitium as factor XIIIa-positive spindle-shaped tumor cells. These c-met expressing cells also produce additional cytokines besides SF, e.g. IL-6 and oncostatin M, that can further expand the ongoing neovascularization process and promote the autocrine and paracrine-mediated growth of KS tumor cells. Furthermore, in the classical form of KS (non-AIDS related), it is believed that transformation of endothelial cells to KS tumors is defined as a rare, retrovirus/T cell independent event. When endothelial cells are "initiated" by a carcinogen i.e. acquisition of a transforming viral sequence, but are not, or perhaps infrequently "promoted" (stimulated to proliferate), rare tumors develop but only after a long latency period. SFs participation in the model is limited to the established KS tumor where it functions to stimulate both tumor cell proliferation and neovascularization. In the HIV-related form of KS, it is believed that KS tumor formation is a retrovirus/T cell dependent process. Endothelial cells that have been "initiated" by transforming viral sequences are now constantly exposed to the growth "promoting" influences of SF produced by retrovirus (HIV) infected T cells. As a consequence, there is clonal expansion of "initiated" endothelial cells which eventually undergo stable, irreversible "phenotypic conversion" to KS tumor cells. This combination of events results in a marked increase in the frequency of tumor formation with a much shorter latency period. Moreover, the continued production of SF by KS tumors insures their sustained proliferation and neovascularization. It is thus believed that SF plays a central role in the etiology and pathogenesis of AIDS-associated KS by 1) inducing phenotypic conversion of endothelial cells that have been "initiated" by transforming sequences such as HIV tat, HPV-16 E6/E7, or the HPV functional homologue SV40 large T antigen; 2) promoting the clonal expansion of phenotypically converted/initiated endothelial cells; and 3) sustaining the growth of established KS by stimulating tumor cell proliferation and neovascularization.

It should be understood that, although models for KS cell growth regulation are described with respect to inhibition or down-regulation, enhancement or up-regulation of KS cell growth is also in accordance with the principles of the present invention. Up-regulation or enhancement of KS cell growth may be useful for example, in in vitro studies such as treatment efficacy studies. It should also be understood that KS cell growth can refer to extra-cutaneous as well as cutaneous clinical lesions of KS. It is known that in diseases such as HIV-induced psoriasis, angiogenic factors play an important role in the pathogenesis of the disease. It should also be recognized, therefore, that in HIV-induced diseases characterized by angiogenesis and where SF is a contributing factor to the angiogenesis, the present methods of the invention may also be applied.

In practicing the method of the present invention, the amount of biological reagents administered such as antibodies, non-stimulatory ligands and antisense constructs, will vary with the patient being treated and will be monitored on a patient-by-patient basis by the physician. Generally, a therapeutically effective amount in a biologically compatible form suitable for administration in vivo, will be administered for a therapeutically effective duration. By "therapeutically effective amount" and "therapeutically effective duration" is meant an amount and duration effective to achieve a selected desired result in accordance with the present invention without undue adverse physiological effects. By "biologically compatible form suitable for administration in vivo" is meant a form in which the toxic effects, if any, are outweighed by the therapeutic effects. It will be appreciated that administration of the biological reagents of the present invention will be by methods known to those skilled in the art, such as intravenous, subcutaneous and dermal injection, oral ingestion and topical ingestion by vehicle means. It should further be appreciated that both treatment dosage and duration will be interdependent and can be varied together in order to achieve an optimal clinical response. It should also be appreciated that the various methods of the present invention may be combined by those skilled in the art to achieve an optimal clinical response.

The following Specific Examples describe in further detail the present invention.

SPECIFIC EXAMPLE 1

Materials and Methods

Cell Lines. Four different KS tumor cell lines were isolated from skin (KS-I and KS-II), ocular conjunctiva (KS-III), and pleural effusion (KS-IV) of AIDS patients and grown in KS cell growth medium (KSGM) according to the method described by Huang, et al. (Huang, Y. et al., Arch. Dermatol. 129:1291–1296 (1993)). Human umbilical vein endothelial cells (HUVECs) and human arterial smooth muscle cells (HASMCs) were provided by Dr. S. Zaki Salahuddin (Institute of Molecular Medicine and Technology, University of Southern California, Los Angeles, Calif.). Madin-Darby canine kidney (MDCK) cells were obtained from Dr. Stephen Warren (Department of Pathology, Yale University School of Medicine, New Haven, Conn.).

Cell Culture. KS cells were isolated and cultured in KSGM, which is composed of RPMI-1640 (Gibco, Gaithersburg, Md.) plus fetal calf serum (15% (v/v)) (Hyclone, Logan, Utah), Nutrodoma-Hu (5% (v/v)) (Boehringer-Mannheim, Indianapolis, Ind.), and conditioned medium from the HTLV-II infected human T lymphocyte line 38–10 (20% (v/v)) (provided by Dr. Parkash Gill, Institute of Molecular Medicine and Technology, University of Southern California). HUVECs were cultured in HUVEC growth medium, which consists of Ham's F-12 and Iscove's modified Dulbecco's medium (1:1) (Gibco) plus fetal calf serum (20% (v/v)), endothelial cell growth factor (30 ug/ml), and heparin (20 U/ml) (Sigma Chemical Co., St. Louis, Mo.). KS cells and HUVECs were grown in tissue culture flasks coated with 2% gelatin (Sigma), subcultured at weekly intervals using trypsin, and re-seeded at a 1:4 split ratio. HASMCs and MDCK cells were cultured in Dulbecco's Modified Eagle's Medium (DMEM) containing 10% fetal calf serum, as described earlier (Rosen, E. M. et al., Proc. Soc. Exp. Biol. Med. 195:34–43 (1990)). Cells were incubated in a humidified atmosphere of 95% air and 5% $CO_2$ at 37° C. For proliferation assays, KS cells were initially seeded into 48 well dishes in KSGM, allowed to attach overnight, and then washed three times over the next 6 hr with RPMI-1640. Next the KS cells were incubated either in KSGM or RPMI-1640 plus 10% FCS supplemented with the indicated cytokines or growth factors. After 80 hr, cell counts were manually performed using a hemocytometer. In some experiments, the KSGM was preincubated with 1:200 dilution of SF neutralizing rabbit antibody (Ab 978), or control normal rabbit serum, for 2 hr at 37° C. prior to addition to the washed KS cells. Duplicate counts were performed on duplicate wells and results expressed as mean +/– standard deviation.

Factor XIIIa and B-Actin. Total cell RNA was isolated by acid guanidinium isothiocyanate-phenol-chloroform extraction. The mRNAs in the extract were reverse transcribed into cDNAs with oligo d(T) as primer, in the presence of 0.2 mM dNTPs and MoMuLV reverse transcriptase (Gibco-BRL). Equal amounts of cDNA were subjected to 35 cycles of PCR amplification. The reaction mixture contained 2.5μ taq polymerase, 2.5 mM $MgCl_2$, 0.25 mM dNTPs (Perkin-Elmer Cetus, Branchburg, N.J.), and 20 pM each of 5' and 3' primers. Each cycle consisted of denaturation at 94° C. for 1 min, followed by 1 min of annealing and extension at 62° C. for factor XIIIa (outer primers), and 65° C. for factor XIIIa (internal primers) and B-actin. PCR reactions were subjected to one cycle of denaturation at 9° C. for 3 min before the first cycle, and one cycle of annealing/extension at 72° C. for 7 min at the end. All reactions were subjected to the hot-start PCR method, as described by Chou et al. (Chou, Q. et al., *Nucleic Acids Res.* 20:1717–1720 (1992)). The PCR products were extracted with chloroform, precipitated, analyzed on a 3% agarose gel, stained with ethidium bromide, and visualized under ultraviolet illumination. The validity of the amplified product was ensured by using nested PCR primers specific for factor XIIIa mRNA and by including control reactions lacking various reagents and cDNA. B-Actin was utilized as a control for loading. The Genebank base pair (bp) sequence numbers (5'-3') for the PCR primers used were: factor XIIIa internal primers, 1999–2020 and 2244–2224; B-actin primers, 1259–1278 and 2374–2351. The expected sizes of the amplified sequences are 245 bp for factor XIIIa and 531 bp for B-actin.

HGF/SF and c-met. The mRNAs were reverse transcribed into first strand cDNA as described by Yang et al. (Yang, X. M. et al., *Dev. Biol.* 157:308–320 (1993)). To amplify an HGF/SF specific product of 612 base pairs, two primers corresponding to positions 838–856 and 1429–1450 of the sequence HsHGFHL (EMBL Database accession number M60718) were used in a PCR. Amplification was performed by 45 cycles at 94° C. (1 min), 48° C. (2 min), and 72° C. (2 min) in a Perkin/Elmer Cetus DNA Thermal Cycler. An oligonucleotide corresponding to position 1105–1124 was radiolabeled with d-$^{32}$P)ATP using polynucleotide kinase and hybridized to a blot of the gel used to analyze the fragments. This procedure as well as the control reactions conducted, ensured the validity of the amplified products. To amplify a c-met specific fragment, primers corresponding to positions 2257–2274 and 2557–2574 of the sequence HsMETPAO (EMBL Database accession number J02958) were used. Amplification was performed by 45 cycles at 94° C. (1 min), 45° C. (2 min), and 72° C. (2 min).

Cytokines and Cytokine-Regulated mRNAs. PCR amplification was performed as described by Chou et al. (Chou, Q. et al., *Nucleic Acids Res.* 20:1717–1720 (1992)). The Genebank base pair sequence numbers (5'-3') for the PCR primers used were: interleukin-1 B (LI-1B), 393–412 and 639–628; IL-6, 148–167 and 342–321; IL-8, 75–95 and 375–343; intercellular adhesion molecule-1 (ICAM-1), 1246–1466 and 1594–1586; LI-10, 313–339 and 664–639; granulocyte macrophage colong-stimulating factor (GM-CSF), 36–56 and 472–449; transforming growth factor type alpha (TGF-alpha), 35–58 and 522–495; TGF-Beta, 1678–1697 and 2006–1994.

Immunohistochemical Staining of Cell Cultures. Cells grown in 8-well Lab Tek chambers (VWR Scientific, Chicago, Ill.) were washed with phosphate-buffered saline and fixed with acetone for 5 min. Cells were stained using a sensitive avidin-biotin immunoperoxidase technique (Vectastain Kit, Vector Labs, Burlingame, Calif.), and counterstained with 1% hematoxylin as previously described. Nickoloff, B. J. et al., *Am. J. Pathol.* 135:793–800 (1989). The chromogen, 3-amino-4-ethycarbazole, produced a red reaction product. The primary antibodies used included antibodies against factor XIIIa (1:500) (Calbiochem, La Jolla, Calif.), VCAM01 (1:50) (Genzyme, Cambridge, Mass.), factor VIII-related antigen (a:100) (Dako Corp., Santa Barbara, Calif.), and anti-smooth muscle alpha-actin (1A 4; Sigma Chemical Corp). Control antibody for factor XIIIa was rabbit antiserum against factor XIIIs used at 1:50 dilution (Calbiochem).

Cytospin Preparations. To prepare cytospins, 200 ul of a cell suspension from indicated cultures ($10^6$ cells/ml) were combined with 1% bovine serum albumin and spun onto glass slides (500 rpm, 5 min) using a Shandan-3 instrument (Shandin Inc., Pittsburgh, Pa.).

Tissue Sections. Five um thick cryostat sections of AIDS-KS lesions from five different patients were immunostained using rabbit polyclonal antibodies to human placental SF (Ab 978, 1:1000) (Grant, D. S. et al., *PNAS* (USA) 90:1937–1941 (1993)) or to a C-terminal peptide of the c-met protein (Ab C28, 1:1000) (Bottaro, D. P. et al., *Science* 251:802–804 (1991)) as the primary antibody, as described by Nickoloff et al. (Nickoloff, B. J. et al., *Am. J. Pathol.* 135:793–800 (1989)). Normal rabbit serum (1:1000) served as a negative control.

MDCK Serial Dilution Scatter Assay. SF activity was quantitated using the Madin-Darby canine kidney (MDCK) scatter assay, (Rosen, E. M. et al., *Proc. Soc. Exp. Biol. Med.* 195:34–43 (1990)). Briefly, samples were serially diluted by factors of two (in 15 ul of DMEM) and incubated with one day old colonies of MDCK cells (in 150 ul of DMEM-10% serum) for 20 hr in 96-well plates. Cells were stained and examined for scattering (colong spreading and cell separation). The SF activity at the limiting dilution was defined as 0.5 scatter nits/ml, allowing calculation of the SF titer in the undiluted sample.

Scatter Factor ELISA. Immunoreactive SF protein was quantitated using a double antibody ("sandwich") ELISA. Immulon II 96-well plates (Dynatech, Alexandria, Va.) were coated with a mouse monoclonal to human SF (10C11) (Bhargava, M. et al., *Cell Growth & Diff.* 3:11–20 (1992)) (1:4000 of ascites) in Na $Co_2$ buffer, pH 9.6, overnight at 37° C. Wells were washed ×4 with tris-buffered saline (TBS) (Tris 20 mM, 0.1M NaCl, pH 7.5); blocked with bovine serum albumin (BSA) (3% in TBS, 1 hr at 37° C.); washed ×4 with TBS; incubated for 2 hr at 37° C. with 100 ul of sample or standard (recombinant human SF); and washed again. Wells were then incubated with rabbit antibody to human SF (Grant, D. S. et al., *PNAS* (USA) 90:1937–1941 (1993)) (1:1000) for 1 hr at 37° C. in TBS with 0.05% Tween-20 and 0.5% BSA (TTBSA); washed ×4 in TTBSA; incubated with goat anti-rabbit IgG conjugated to alkaline phosphatase (1:8000) (1 hr at 37° C.) to recognize bound anti-rabbit SF; and washed again. Color was developed using an Immunoselect substrate amplification kit (GIBCO/BRL), and ODs were read at 490 nm on a Dynatech 96-well spectrophotometer. The assay was specific for SF; plasminogen, serum, and a variety of growth factors and cytokines were not cross-reactive. The lower limit of detection was about 0.1 ng of SF in the 100 ul assay volume.

Rat Cornea Angiogenesis Assay. Neovascularization was assayed in the avascular cornea of the rat eye, as described by Polverini et al. (Polverini, P. J. et al., *Lab. Invest.* 51:635–642 (1984)). HTLV-II conditioned medium (CM) was concentrated 20-fold using Centricon-3 filters (Amicon, Inc., Beverley, Mass.), and 5 ul aliquots were combined 1:1 with a sterile solution of Hydron (Interferon Sciences, New Brunswick, N.J.). In some experiments, HTLV-II CM was combined with a 1:200 dilution of SF neutralizing rabbit antibody for 2 hr at 37° C. prior to assay. The Hydron implants were placed into a surgical pocket within rat corneas for 7 days. Responses were scored after carbon perfusion as positive only when sustained ingrowth of new vessels was present. Angiogenesis inhibition studies were performed using both chicken and rabbit antibodies against SF.

Cytokine Preparations. Mouse SF was purified from ras-transformed NIH/2-3T3 cells, as described by Grant et al. (Grant, D. S. et al., *PNAS* (USA) 90:1937–1941 (1993)). Recombinant human SF was provided by Dr. George VandeWoude, Frederick Cancer Center, Frederick, Md. Recombinant human oncostatin M was obtained from Pepro Tech, Rocky Hill, N.J. Recombinant human IL-6 was purchased from Collaborative Research, Bedford, Mass.

Results

All four KS tumor cell lines appeared morphologically similar and grew with a predominantly spindle-shaped morphology. FIG. 1, photos A–F, show the conversion of human endothelium to a KS tumor cell-like phenotype. Cell cultures were immunostained as described in Materials and Methods. Positive cytoplasmic reactivity was indicated by red staining (shown as black in the Figures). KS tumor cells grown in KSGM were stained for factor XIIIa (FIG. 1, photo A) and for VCAM-1 (FIG. 1, photo B). HUVECs were stained for factor XIIIa before (FIG. 1, photo C) and after (FIG. 1, photo D) a 24 hr incubation in KSGM. HUVECs exposed to 250 units/ml of purified native murine SF (FIG. 1, photo E) or to recombinant human SF (FIG. 1, photo F) for 24 hr were stained for factor XIIIa. The magnification of the Figures is ×60.

As shown in FIG. 1, photos A and B, all four lines expressed strong cytoplasmic immunoreactivity for factor XIIIa (FIG. 1, photo A) and for vascular cell adhesion molecule-1 (VCAM-1) (FIG. 1, photo B), two antigenic markers that are expressed by KS cells in vivo and in vitro (Huang, Y. et al., *Arch. Dermatol.* 129:1291–1296 (1993)). These KS cells were negative for the endothelial cell markers factor VIII antigen, ELAM-1, and factor XIIIs (data not shown). HUVECs cultured in HUVEC growth medium grew with an epithelioid configuration, expressed strong immunoreactivity for factor VIII antigen, and were uniformly negative for factor XIIIa, as shown in FIG. 1, photo C, and for VCAM-1 (data not shown). However, after incubation for 18–24 hr in KSGM, HUVECs became spindle-shaped and acquired immunoreactivity for factor XIIIa, as shown in photo D, and for VCAM-1 (data not shown).

No significant loss of factor VIII expression was detected when HUVECs became spindle-shaped after exposure to KSGM. In contrast, HASMCs were negative for factor XIIIa before and after exposure to KSGM. These cells remained positive for the smooth muscle marker alpha-actin. HUVECs could be passaged in KSGM multiple times over 5–6 weeks. These "phenotypically converted" HUVECs appeared healthy and divided, although at a slower rate than the parental cells. When converted HUVECs were returned to HUVEC growth medium, they reverted to their original epithelioid morphology over a one week period. This in vitro phenomenon may parallel the in vivo phenomenon of spontaneous regression of KS lesions. Converted HUVECs continued to express factor VII, and morphologically "reverted" HUVECs continued to express factor XIIIa.

Figures 2A, 2B, 2C:
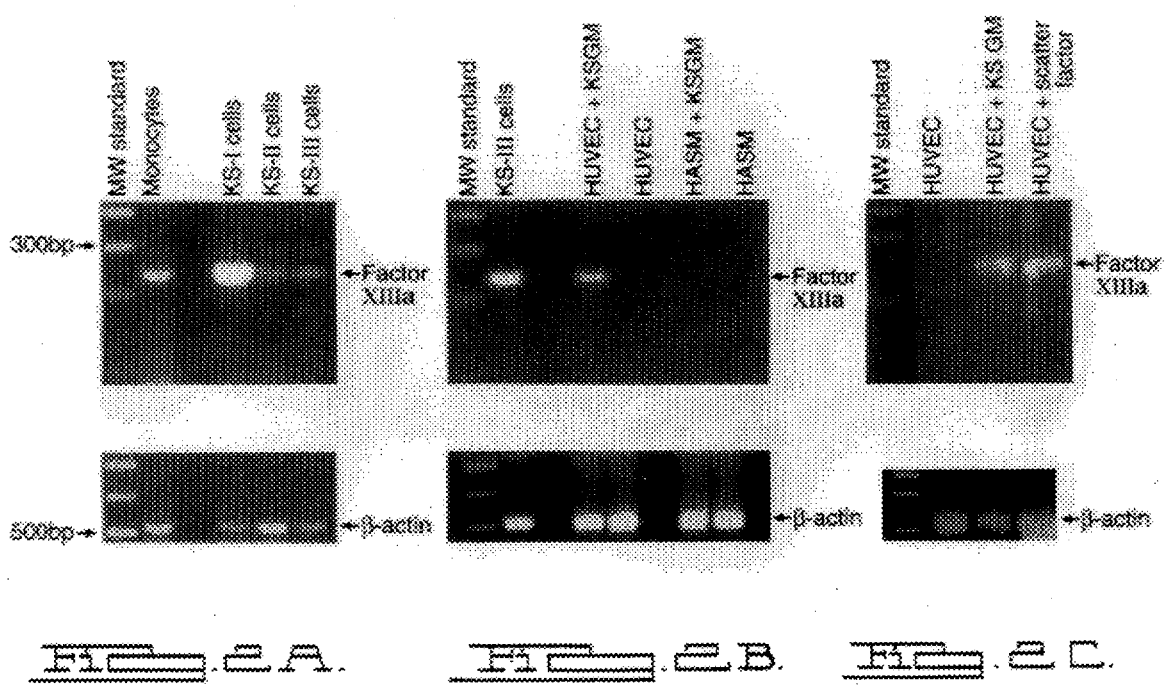
FIG. 2, photos A-C, are photographs of gels showing the PCR analysis of factor XIIIa transcripts.

PCR analysis was used to confirm the presence of factor XIIIa mRNA in cells showing positive immunoreactivity. Human peripheral blood monocytes, a cell type known to express factor XIIIa, served as a positive control (Henriksson, P. et al., *J. Clin. Invest.* 76:528–534 (1985)). FIG. 2, photos A–C, show the PCR analysis of factor XIIIa transcripts. PCR amplification of mRNAs for factor XIIIa and for β-actin (a control for loading) were performed as described in Materials and Methods. FIG. 2, photo A, shows the constitutive expression of factor XIIIa mRNA in monocytes, a positive control, and in three different lines of KS tumor cells. FIG. 2, photo B, shows the expression of factor XIIIa mRNA in HUVECs and HASMCs before and after a 24 hr exposure to KSGM. FIG. 2, photo C, shows the effect of a 24 hr exposure to murine SF (100 units/ml) on expression of factor XIIIa mRNA by HUVECs.

As shown in FIG. 2, photo A, three of three KS cell lines tested expressed factor XIIIa mRNA. HUVECs did not constitutively express factor XIIIa mRNA. However, after exposure to KSGM, these cells contained easily detectable factor XIIIA mRNA as shown in FIG. 2, photo B. FIG. 2, photo B, also shows that HASMCs did not contain detectable constitutive XIIIa mRNA and could not be induced to express factor XIIIa mRNA by exposure to KSGM (FIG. 2, photo B). Thus, the results of the PCR analysis were in complete agreement with the immunochemical staining profiles.

Figure 3:
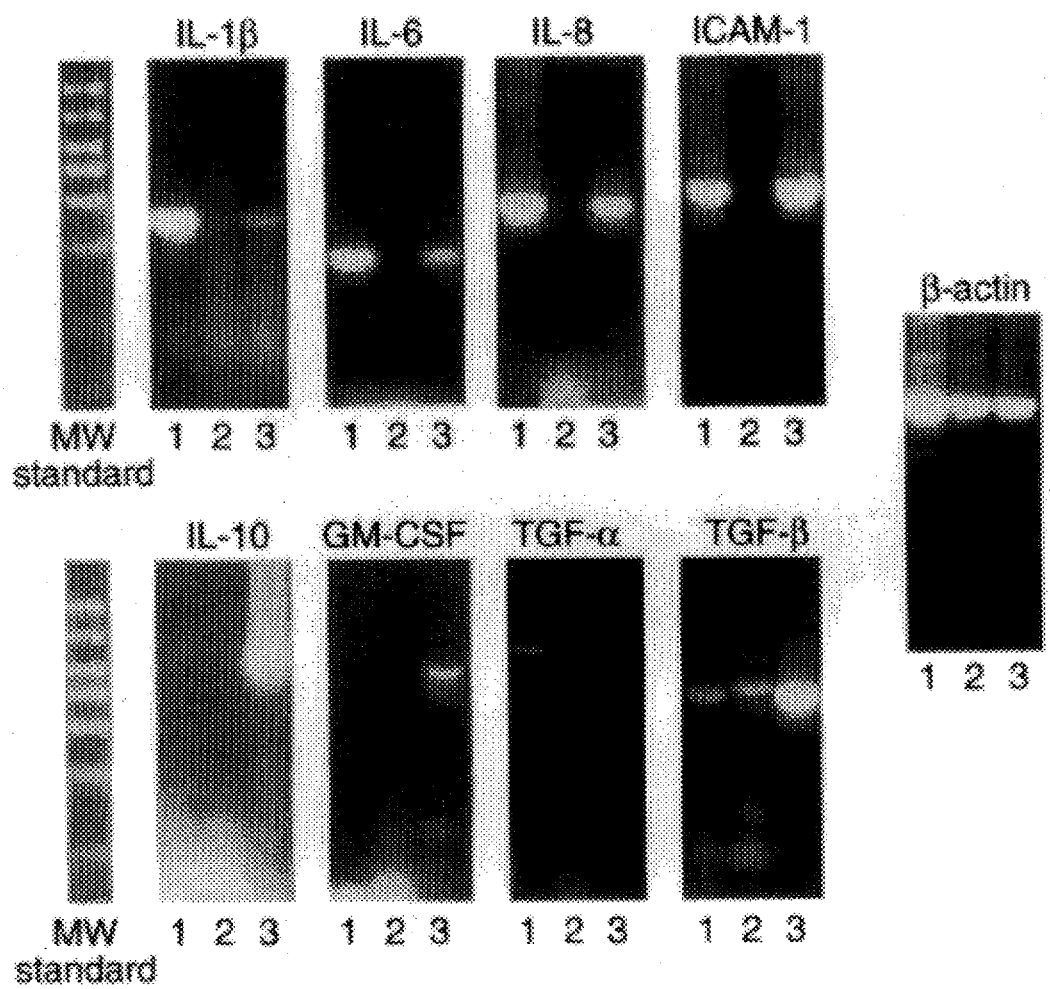
FIG. 3 is a photograph of a gel showing the PCR analysis of cytokines and cytokine-regulated factors.
Figure 4A:
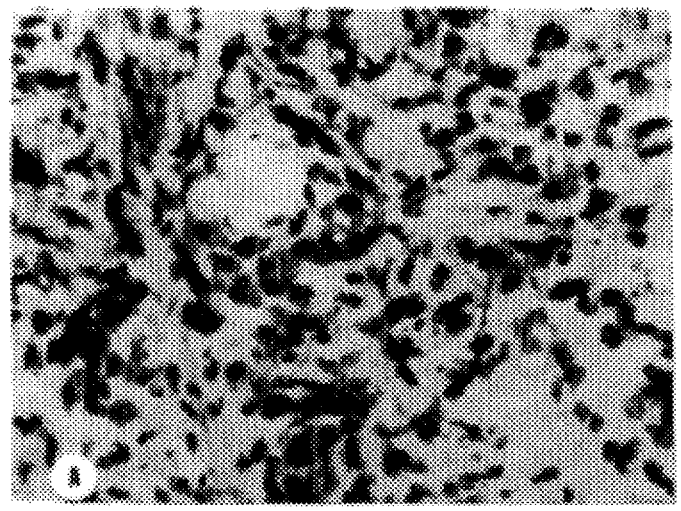
FIG. 4, photos A-F, are photographs showing immunohistochemical detection of scatter factor and its cell surface receptor in KS lesions in vivo and in cultured cells.
Figure 4B:
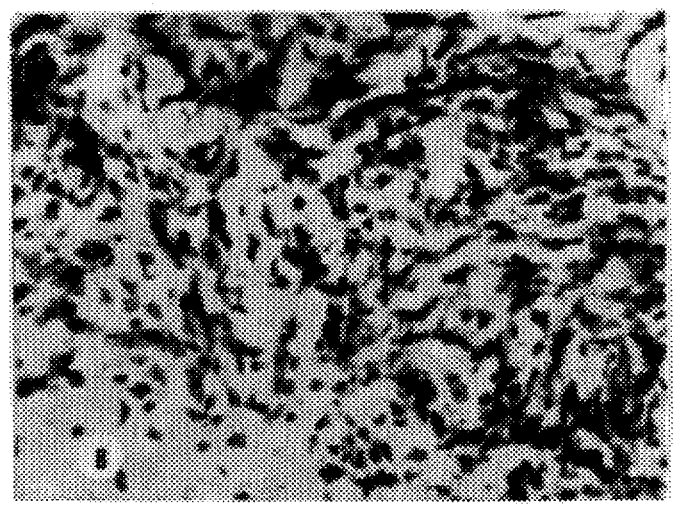
Figure 4C:
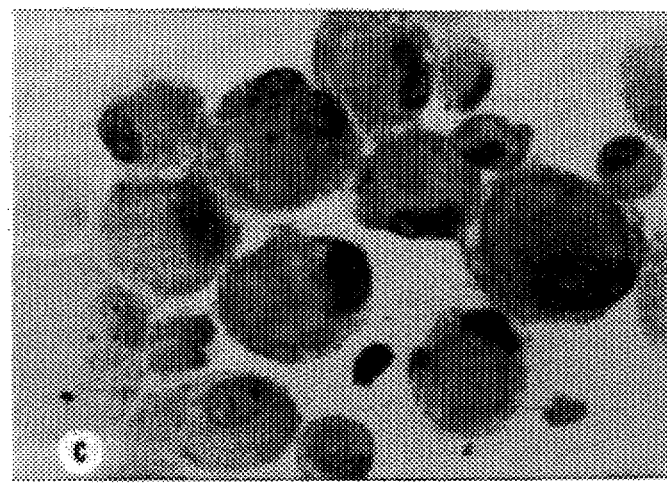
Figure 4D:
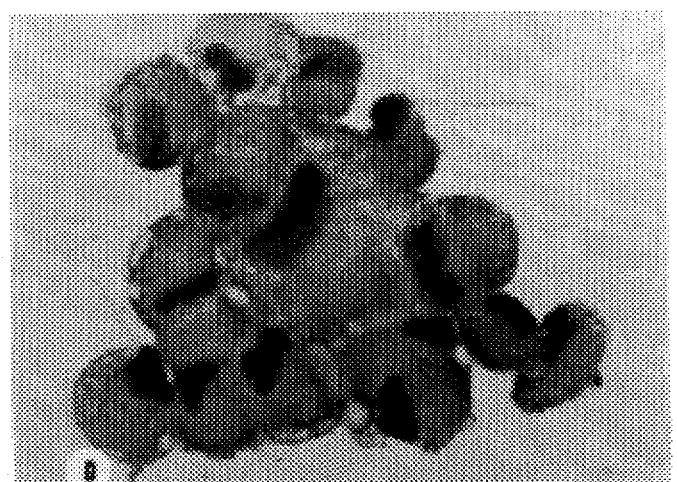
Figure 4E:
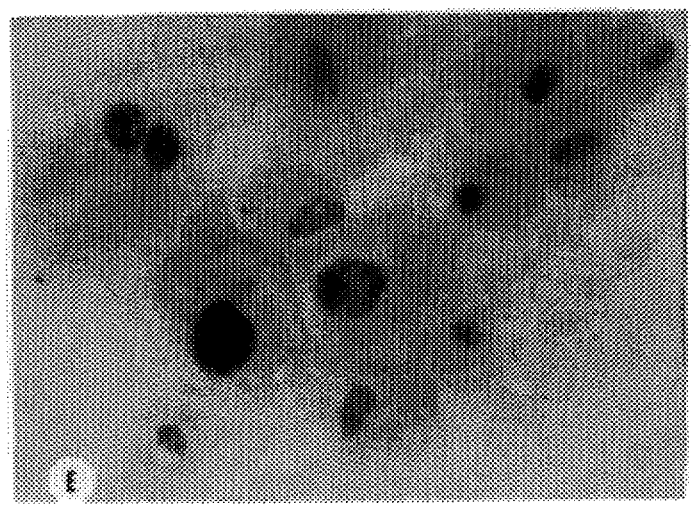
Figure 4F:
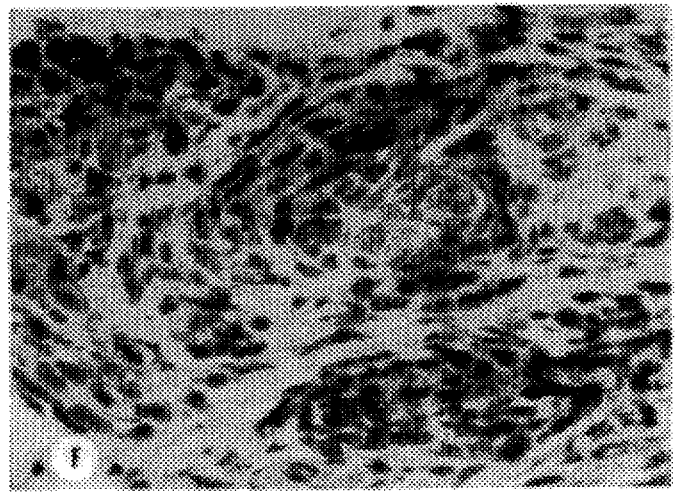

It has been suggested that a disordered cytokine network may contribute to the development of KS lesions (Nakamura, S. et al., *Science* 242:425–430 (1988) and Vogel, J. et al., *Nature* (London) 335:606–611 (1988)). The expression of mRNAs encoding a number of cytokines and cytokine-regulated adhesion and growth factors was thus examined. The expression of mRNAs that encode various cytokines and cytokine-regulated factors was determined by PCR analysis. Results are shown for KS tumor cells that were isolated and cultured in KSGM (lane 1 of FIG. 3), control HUVECs that were cultured in HUVEC growth medium (lane 2 of FIG. 3), and "phenotypically converted" HUVECs following exposure to KSGM for 24 hr (lane 3 of FIG. 3). As shown in FIG. 3, when HUVECs were phenotypically converted to KS-like cells by exposure to KSGM, they acquired the ability to express four transcripts (IL-1β, IL-6, IL-8, and ICAM-1) that are also expressed by KS tumor cells. These mRNAs were not expressed constitutively by control HUVECs cultured in HUVEC growth medium. KS cells, HUVECs, and phenotypically converted HUVECs shared the ability to express TGF-β mRNA, as shown in FIG. 3, while none of these cell types expressed mRNAs for IL-2, IL-3, IL-4, IL-5, tumor necrosis factor-alpha, or interferon-gamma (data not shown). However, there was a discrepancy in the expression of IL-10, GM-CSF, and TGF-α among these different cultured cells. Thus, endothelial cells can be converted into cells that clearly resemble cultured KS tumor cells by morphologic, immunophenotypic and functional criteria.

Since SF converts epithelial cells to a spindle-shaped morphology, analogous to the effect of KSGM on endothelial cell morphology, KSGM was assayed for the presence of SF. Very high titers of SF activity in conditioned medium from the HTLV-II-infected human T cell line 38-10 (HTLV-II CM) was detected. This conditioned medium is an essential component of KSGM. No SF was detected in any other component of KSGM. Two batches of HTLV-11 CM contained 218 and 154 scatter units/ml, using a sensitive and specific bioassay of SF (Rosen, E. M. et al., *Proc. Soc. Exp. Biol. Med.* 195:34–43 (1990)). High levels of SF antigen in HTLV-II CM (10.5 ng/ml) were also found, using a double antibody ELISA. The SF production rate for 38-10 cells was estimated to be about 120 units/$10^6$ cells/48 hr., as compared with 20–80 units/$10^6$ cells/48 hr. for six different human fibroblast lines. PCR analysis confirmed that 38-10 cells express SF mRNA (data not shown). In contrast, CM from purified, resting human T cells and from the HUT 78 human T cell line contained no detectable SF by bioassay or ELISA. These findings show that retrovirus-infected human T cells can produce very large quantities of SF.

After exposure to purified native mouse SF or recombinant human SF for 12–18 hr., HUVECs became spindle-shaped and expressed immunoreactive factor XIIIa, as shown by FIG. 4, photos E and F, and factor XIIIa mRNA, as shown by FIG. 2, photo C. In addition, rabbit antibody to human SF blocked the KSGM-induced phenotypic conversion of HUVECs. Thus, SF appears to be the essential cytokine required for the morphologic and immunophenotypic conversion of endothelial cells to a KS cell-like phenotype. These findings suggest that SF plays a significant role in the biology of KS.

KS lesions were examined for the presence of SF in vivo. FIG. 4, photos A–F, show immunohistochemical detection of scatter factor and its cell surface receptor, the c-met protein, in KS lesions in vivo and in cultured cells. Cryostat sections of AIDS-KS lesions were immunostained using polyclonal rabbit antibodies to human placental SF (FIG. 4, photos A and B), or to a C-terminal peptide of the c-met protein (FIG. 4, photo F) as the primary antibodies. Cytospin preparations of culture KS tumor cells (FIG. 4, photos C and E) and HUVECs (FIG. 4, photo D) were stained with anti-c-met antibody (FIG. 4, photos C and D) or with normal rabbit serum as a control (FIG. 4, photo E), Results portrayed by FIG. 4, photos A–F, are representative of five different KS lesions and three different KS cell lines.

As shown in FIG. 4, photos A and B, KS lesions from five patients showed positive immunostaining for SF in round lymphoid cells, perivascular dendritic cells, and interstitial spindle-shaped cells, but not in endothelial cells. Similar results were obtained using rabbit polyclonal antibody or mouse monoclonal antibody (10C11) (Bottaro, D. P. et al., *Science* 251:802–804 (1991)) against human placental SF. The receptor for SF has been identified as the c-met proto-oncogene protein product, a transmembrane growth factor receptor-like tyrosine kinase (Bottaro, D. P. et al., *Science* 251:802–804 (1991)). As shown in FIG. 4F, a variety of cell types in the KS lesions stained positively for c-met protein, including pericytes, pill-erector muscle bundles, endothelial cells, dermal cells, and interstitial spindle-shaped tumor cells. Moreover, as shown by FIG. 4, photos C, D and E, cytospin preparations of cultured KS tumor cells (FIG. 4C) and HUVECs (FIG. 4, photo D) were positively stained by antibody to c-met but not by control antibody (FIG. 4, photo E). In addition, cultured bovine pericytes (provided by P. D'Amore, Harvard Medical School), HUVECs, and three out of three KS tumor cell lines expressed c-met mRNA by PCR analysis.

Figure 5A:
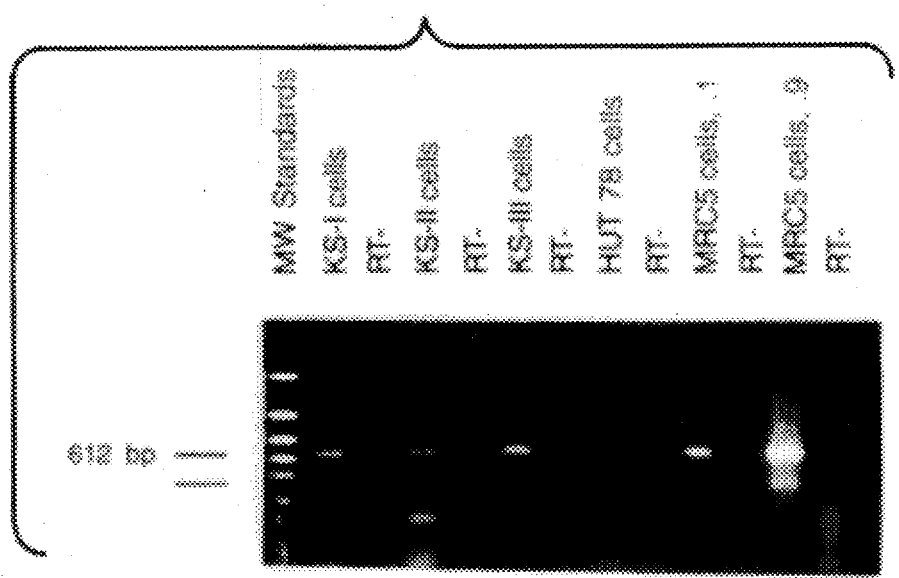
FIG. 5, photos A and B, are photographs of gels showing KS tumor cell expression of SF mRNA.
Figure 5B:
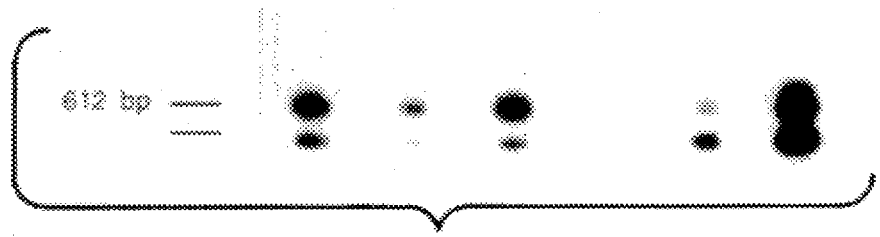
Figure 8:
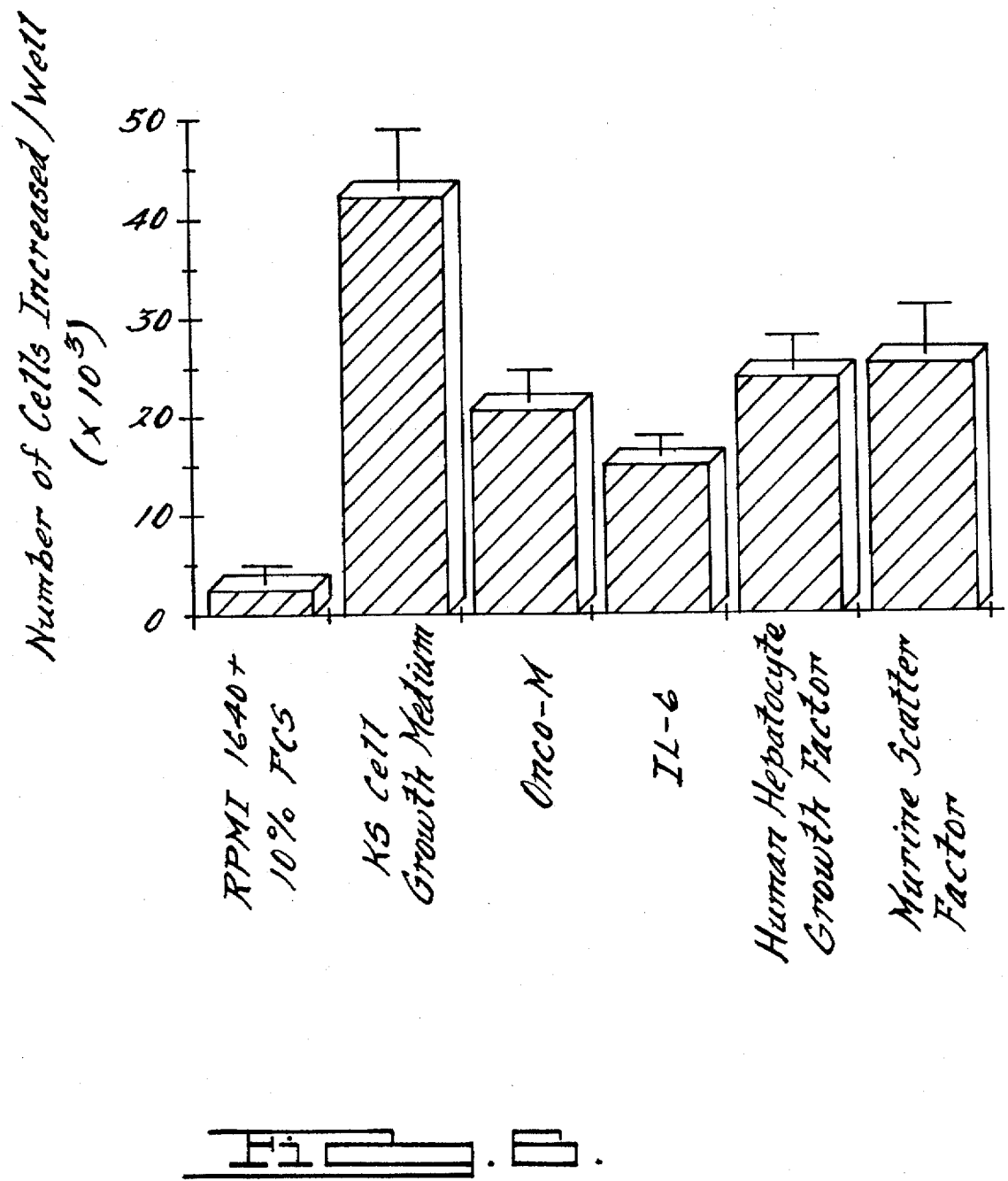

FIG. 5, photos A and B, show KS tumor cell expression of SF mRNA. PCR amplification of mRNAs for SF was performed as described in Materials and Methods. The ethidium bromide stained gel in FIG. 5, photo A, shows the expression of SF mRNA in MRC5 cells, a positive control (0.1 of a full PCR, and 0.9 of the same PCR), in three different lines of KS tumor cells, and no expression in HUT 78 cells, a negative control. First-strand cDNA synthesis was performed with and without reverse transcriptase (RT⁻). The last lane (-) of FIG. 5, photo A, represents a control where no cDNA template was used in the PCR amplification. FIG. 5, photo B, shows the same gel after blotting and hybridizing with an internal radiolabeled SF oligonucleotide primer. The 612 bp SF specific product is indicated, as well as a fragment that is consistently detected in different cell lines, and that is thought to be derived from a smaller isoform of SF mRNA. Molecular weight standard fragments shown are 1444, 955, 736, 585, 476, 341, 258, and 144 bp.

The presence of SF in KSGM and in KS lesions in vivo and KS cell lines in vitro suggested that SF might be a growth factor for KS cells. FIG. 6 shows the effect of scatter factor on KS tumor cell proliferation. 25,000 KS cells were seeded into 48-well plates and allowed to attach overnight. Cells were washed ×3, incubated in 0.5 ml RPMI-1640 plus 10% fetal calf serum containing different factors for 80 hr and counted. Cytokines were used at doses sufficient to give maximal proliferative responses: recombinant human SF(HGF), 250 units/ml; purified native mouse SF, 250 units/ml; recombinant human oncostatin M, 100 ng/ml; recombinant human IL-6, 500 U/ml. Results portrayed in FIG. 6 are representative of three different experiments and the values are means +/− standard deviations of duplicate assays.

As shown by FIG. 6, three of three KS tumor cell lines tested were stimulated to proliferate by both mouse and human SF. Dose-response studies showed little or no stimulation or proliferation of KS cells at 10 units/ml, near maximal stimulation at 100 units/ml, and maximal stimulation at 250 units/ml of human SF. As shown by FIG. 6, SF appeared to be at least as potent as two known KS tumor cell mitogens, IU6 (Miles, S. A. et al., *PNAS* (USA) 87:4068–4072 (1990)) and oncostatin M (Miles, S. A. et al., *Science* 255:1432–1434 (1992)), although none of these three factors were as potent as KSGM. Combinations of saturating concentrations of SF, oncostatin M, and IL-6 did not yield additional stimulation of proliferation.

Figure 7:
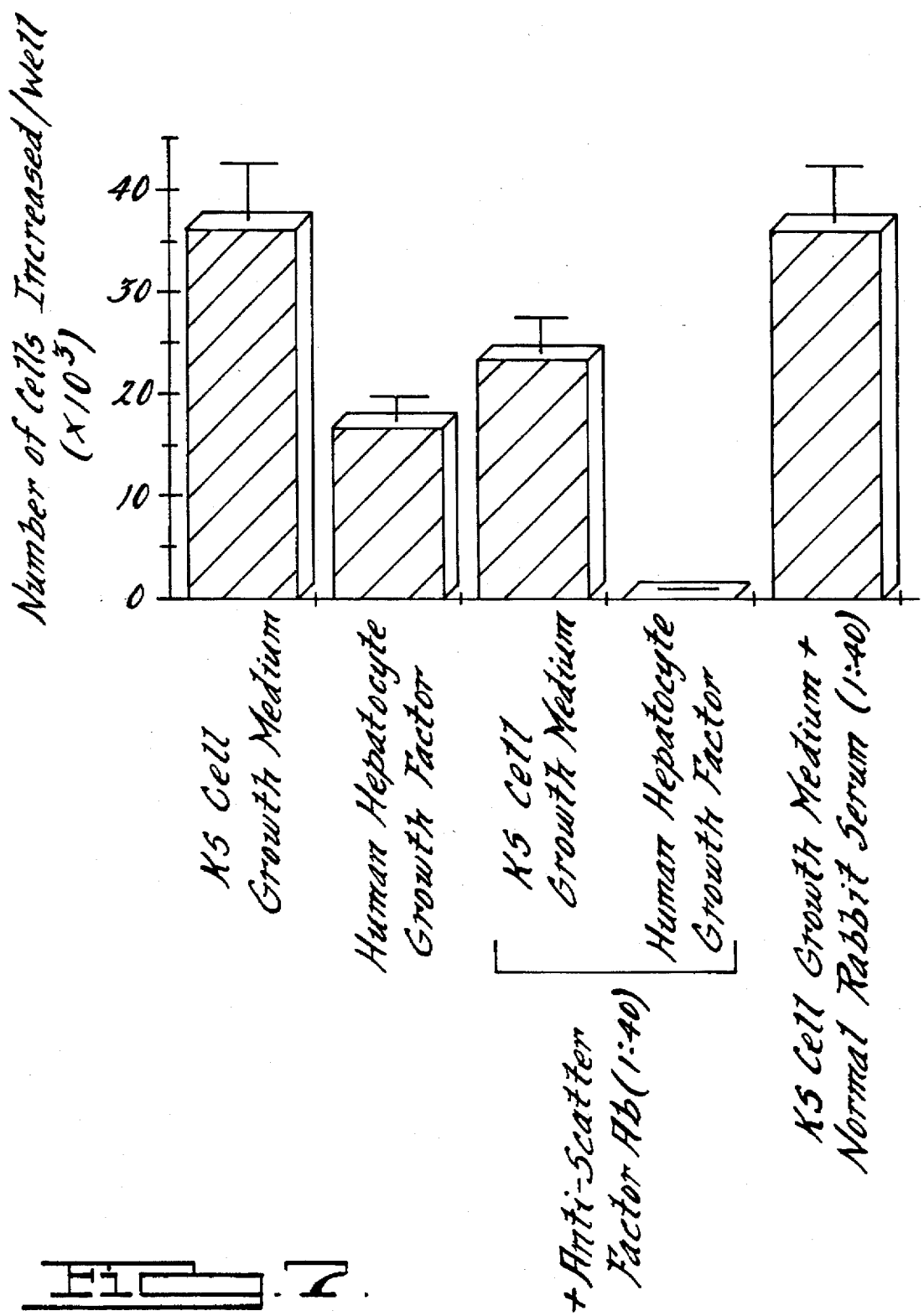
FIG. 7 is a graph showing the blocking of KS cell growth by antibody against scatter factor.

To assess the relative mitogenic contribution of SF in KSGM, neutralizing antibody (Ab) to SF was added to KSGM, and the subsequent proliferation of KS cells measured. As a positive control, the rabbit neutralizing antibody was used with recombinant human HGF, and blocked virtually 100T of the subsequent growth stimulation as shown by FIG. 7. FIG. 7 shows blocking of KS tumor cell proliferation by anti-SF antibody. The proliferation assay was performed as described above except that growth medium was pre-incubated with either rabbit anti-SF antibody, or normal rabbit serum for 2 hr at 37° C. prior to initiating the proliferation assay. The results of a representative experiment is portrayed by FIG. 7.

In three KS cell lines tested, when KSGM was preincubated with rabbit anti-SF antibody (at 1:40), the KSGM-induced proliferation was reduced between 9% and 46%. As illustrated by FIG. 7, there was no inhibition of KSGM-induced proliferation when normal rabbit serum was substituted at 1:20 dilution. FIG. 7 also shows that when the rabbit anti-SF antibody was further diluted beyond 1:400, no inhibition of KS cell growth was observed.

Endothelial cell proliferation and neovascularization are common features of the KS lesion. The angiogenic activity of KSGM and relevant positive/negative control cytokines was investigated and the results are summarized below in Table 1, which show inhibition of angiogenesis induced by KSGM using anti-SF antibodies. The rat corneal neovascularization assay was used to assess the pro-angiogenic properties of KSGM with respect to SF. Both positive and negative controls were performed, and both chicken and rabbit anti-SF antibodies could effectively reduce the majority of angiogenesis induced by KSGM.

TABLE 1

| Content of Hydron Pellet | Corneal Neovascularization | |
|---|---|---|
| | Positive Responses | % |
| Controls | | |
| PBS | 0/3 | 0 |
| bFGF (100 ng) | 3/3 | 100 |
| rhHGF (100 ng) | 2/2 | 100 |
| KS CM | 4/4 | 100 |
| Chicken anti-HGF Ab | 0/4 | 0 |
| Rabbit anti-HGF Ab | 0/3 | 0 |
| bFGF (150 ng) + rabbit Ab | 0/3 | 0 |
| KS growth Medium + Ab | | |
| rhHGF (100 ng) + chicken Ab (1:20) | 1/3 | 33 |
| rhHGF (100 ng) + rabbit Ab (1:200) | 1/5 | 20 |
| KS CM + chicken Ab | 2/5 | 40 |
| KS CM + rabbit Ab | 1/4 | 25 |

Compared to known angiogenic cytokines such as bFGF and HGF, KSGM HTLV-II CM was highly angiogenic in the rat cornea angiogenesis assay (Polverini, P. J. et al., *Lab. Invest.* 51:635–642 (1984)), with 4 out of 4 strongly positive corneal neovascular responses. This angiogenic activity was reduced by 75% (2 out of 8 positive responses) in the presence of rabbit antibody to human SF (used at 1:200 dilution for 2 hr at 37° C.), and reduced by 60% using the chicken antibody to SF. Both anti-SF antibodies could neutralize recombinant human HGF induced angiogenesis, and did not cross-react with bFGF. These findings are consistent with a previous study demonstrating that SF is a potent angiogen in vivo (Grant, D. S. et al., *PNAS* (USA) 90:1937–1941 (1993)). Thus, SF appears to be a key factor in KSGM, with growth-promoting activity for KS tumor cells as well as pro-angiogenic activity.

Discussion

Conditioned medium from CD4 antigen positive T lymphocytes infected with certain human retroviruses (HTLV-I, HTLV-II, HIV-1 and HIV-2) is known to support the growth and long-term culture of AIDS-KS-derived tumor cells. (Nakamura, S. et al., *Science* 242:425–430 (1988)). The present invention demonstrates that cultured, normal, human endothelial cells can be converted to a KS tumor cell-like phenotype by treatment with conditioned medium from HTLV-II infected T lymphocytes. The resemblance between phenotypically converted endothelial cells and KS tumor cells is striking, based on similarities in multiple morphologic, immunophenotypic, and functional features. Because endothelial cells exposed to KSBM, together with KS tumor cells, and dermal dendrocytes all share factor XIIIa expression, this immunophenotypic link suggests that these cell types may be more inter-related than previously thought. (Nickoloff, B. J. et al., *Science* 243:1736–1737 (1989)). Indeed a growing body of evidence points to phenotypic diversity and biological potential of endothelial cells derived from the skin (Karasek, M. A. In *Dermal Immune System* Nickoloff, B. J. ed CRC Press, Boca Ratan, pp. 149–162 (1992)).

Despite the similarities between phenotypically converted endothelium and KS tumor cells, these two cell types were not identical. Converted endothelial cells continued to express factor VIII antigen, which is not expressed by KS cells, and showed a few differences in the cytokine production profile relative to that of KS cells. Conditions that would induce KS cells to acquire endothelial cell markers, such as factor VII or ELAM-1 (Huang, Y. et al., *Arch. Dermatol.* 129:1291–1296 (1993)) have not yet been found. Thus, HTLV-II CM appears to mediate at least the initial phases of the transdifferentiation of endothelium into KS tumor cells. Cytokines and/or cell-cell interactions missing from the culture environment are likely to be required to complete the transformation process.

Large quantities of SF in the conditioned medium from HTLV-II infected T cells was detected, but not from resting or uninfected T cells. The present invention shows that the ability of HTLV-II CM to convert endothelial cells to a KS cell phenotype is due, in great part, to SF. The present invention further demonstrates that HTLV-II CM is highly angiogenic in the rat cornea angiogenesis assay and that SF is responsible for most of the angiogenic activity.

The major producers of SF include fibroblasts, vascular smooth muscle cells, and macrophages (Rosen, E. M. et al., *In: Cell Motility Factors*, Goldberg, I. D. and Rosen, E. M. eds., Birkhouser-Verlag, Basel, pp. 76–88 (1991)). The present invention establishes that T cells activated by retrovirus infection can also produce significant amounts of SF. In preliminary studies, HIV-1 infected HUT 78 T cells can also produce SF mRNA and protein as determined by Northern blot hybridization, ELISA, and bioassay, although at much lower levels compared to the HTLV-II infected 38-10 T cells. Immunoreactive SF was detected in round lymphoid cells, dendritic cells and KS tumor cells, but not in endothelial cells, in vivo. This finding is consistent with previous observations that perivascular round mononuclear cells and spindle-shaped cells in psoriatic lesions stain positively for SF, but the cells of the blood vessel wall do not stain for SF (Grant, D. S. et al., *PNAS* (USA) 90:1937–1941 (1993)). Interestingly, psoriasis like KS is increased in AIDS patients (Nickoloff, B. J. et al., *Science* 243:1736–1737 (1989) and Nickoloff, B. J. et al., *Am. J. Pathol.* 135:793–800 (1989)), and both share a prominent angiogenic response (Folkman, J., *J. Invest. Dermatol.* 59:40–43 (1972)), as well as accumulation of factor XIIIa positive dermal dendrocytes. The presence of SF in dermal dendrocytes and KS cells with KS lesions could result from the uptake or production of SF by these cells. To further distinguish between these possibilities it was observed that three different KS cells in vitro could express SF mRNA. Autocrine production of and response to SF by epithelial cells has been described (Adams, J. C. et al. *J. Cell Sci.* 98:385–394 (1991)). For KS cells, it is also likely that they utilize such an autocrine, as well as paracrine, mechanism of SF-induced growth stimulation because these tumor cells express high levels of c-met. Since KSGM contains other known KS cell mitogens (IL-6, oncostatin M), it is not surprising that anti-SF did not completely inhibit all of the KSGM induced proliferative response. Nonetheless, the present invention clearly demonstrates that SF plays a significant role in stimulating KS cell growth, as well as mediating an angiogenic response.

A variety of endothelial cell lines have been assayed for SF production and none have been found that produce detectable SF activity (Rosen, E. M. et al., *Proc. Soc. Exp. Biol. Med.* 195:34–43 (1990) and Rosen, E. M. et al., *In: Cell Motility Factors*, Goldberg, I. D. and Rosen, E. M. eds., Birkhouser-Verlag, Basel, pp. 76–88 (1991)). However, it has been reported that hepatic sinusoidal endothelium in vivo express SF(HGF) mRNA in response to liver injury (Kinoshita, T, et al., *Biochem. Biophys. Res. Commun.* 165:1229–1234 (1989)). These findings suggest that endothelial cells may be capable of producing SF in response to an, as yet, unidentified stimulus that is present in vivo in the setting of organ damage. Relatively little is known about the signals that initiate and regulate SF production. A protein called "injurin," that is released into the bloodstream within 3–4 hr after liver injury up-regulates expression of SF mRNA in vivo in the lung and other organs. Matsumoto, K. et al., *PNAS* (USA) 89:3800–3804 (1992). Injurin stimulates SF expression in fibroblast cultures, however, it is not clear if injurin also induces SF production in endothelial cultures. If a suitable stimulus were present within KS lesions, then endothelium transformed into KS tumor cells could be capable of producing their own SF.

SPECIFIC EXAMPLE 2

To further investigate the role of SF on KS cell growth, studies are performed in tat transgenic mice and in mice with SV40-transformed EC tumors. The cellular source of SF/c-met, its tissue distribution, and its temporal and spatial pattern of expression is determined in the studies. PCR analysis, in situ hybridization and immunostaining is used. In particular, a phenotypic analysis of KS tumors in tat transgenic mice and in transplanted SV40-transformed endothelial cell (EC) tumors is performed. The SV-40 transformed EC line when implanted into nude mice readily invades surrounding tissues, metastasizes widely and is lethal. This tumor bears a striking resemblance to authentic KS tumor in humans and is thus an excellent human KS model. The SV40 transformed EC tumor line prior to initiating transplant experiments is phenotyped, to confirm the KS phenotype, and is also phenotyped following transplantation into nude mice.

To further investigate production of SF, the above animal models are studied to determined if the KS cytokine panels (discussed above) as well as IL-1 and TNF-α are expressed in emerging KS tumors in tat transgenics and in SV40 tumors transplanted into nude mice. Whether there is a corresponding increase in SF/c-met expression in tumors and associated host cells is also determined. Relevant cytokines are injected into emerging tat mouse KS tumors and into sites of implanted SV40 EC tumors to determine if SF/c-met is unregulated and if this correlates with: 1) an increase in the incidence of spontaneous KS tumors in tat transgenics; and, 2) an increase in the rate of growth of SV40-EC tumors in nude mice. If one or more cytokine is associated with the up-regulation of SF/c-met, neutralizing antibodies to these cytokines are injected into tumors to determine (by PCR analysis, in situ hybridization and immunostaining) if SF/c-met expression is down-regulated. The relationship between tumor incidence and growth is also determined.

Experiments are also performed to further study the effect of SF on the induction and acceleration of the emergence of KS lesions in tat transgenic mice, the enhanced growth of KS-like tumors implanted into nude mice and, the reversal of tumor incidence and growth with antibodies to SF or c-met. In particular, microgram quantities of SF are introduced subcutaneously by 1) direct injection; 2) implanting Hydron pellets containing SF; and 3) systemically via tail vein injection. In each of these experiments, growth is visually monitored and thymidine uptake by tumor cells is measured.

In particular, to study the effects of SF on induction or acceleration of tumor growth, SF is introduced into the skin of tat mice at single and multiple sites prior to the emergence of tumors. To study the effects of SF on increasing the incidence of SV40 EC tumor-take, single or multiple doses of SF are injected into the skin of nude mice immediately before the injection into SV40 EC tumors cells. Finally, to study the effect of SF on acceleration tumor growth in both models, single or multiple doses of SF are injected directly into early tumors. SF is also introduced by incorporation into slow release Hydron and implant pellets that are placed subcutaneously adjacent developing tumors. SF is also introduced via systemic tail vein injection, once again into tat mice that are tumor free and into tat mice that already have tumors.

Antibodies to SF and its receptor c-met, are also injected to study tumor regression. Polyclonal antibodies to SF and c-met are directly injected into tumors in both animal models and tumor growth is monitored visually and microscopically.

The following is a more detailed description of one study of the present invention.

The effects of anti-SF in inhibiting tumor cell growth in mice over a 100 day period at various anti-SF doses is examined. SV-40 transformed murine endothelial cells are injected into the skin of a nude mouse. The injection produces a skin tumor with many clinical and histological features resembling KS. O'Connell, K. A. et al., *Am. J. Pathol.* 139:734–749 (1991) and O'Connell, K. A. et al., *J. Invest. Dermatol.* 100:742–745 (1993). At various stages of the evolution of these KS-like tumors following injection of the endothelial cells, it is determined if neutralizing antibody against SF inhibits tumor cell growth in vivo. The experiment includes 5 animals in each of the following groups:

|  | Day 0 | Day 1 | Day 10 | Day 20 | Day 30 | Day 40 | Day 50 | Day 100 |
| --- | --- | --- | --- | --- | --- | --- | --- | --- |
| Group 1: Control (No Ab) | | | | | | | | |
| Group 2: Anti-SF Ab, 3 doses | X | X | X | | | | | |
| Group 3: Anti-SF Ab, 6 doses | X | X | X | X | X | X | | |
| Group 4: Murine IFN-α, 6 doses | X | X | X | X | X | X | | |
| Group 5: PBS, 6 doses | X | X | X | X | X | X | | |

IFN-α is used as the positive control, because clinical efficacy for IFN-α in the treatment of human KS patients has been observed.

After 100 days, tumor size is measured and the animals are sacrificed to permit detailed histological analysis of KS tumors. Quantitative comparisons are made between control group 1, and the other four groups. Statistical evaluation includes Student's t-test (two-sided) between control group 1 and other groups, and differences are considered significant if $p<0.01$.

The following materials and methods further detail the studies set forth above.

Materials and Methods

Cell Lines. Both HUVECs and MVECs have been isolated. Nickoloff, B. J. et al., *Arch. Dermatol. Res.* 280:235–245 (1988). Once the ECs are isolated from either umbilical vein or skin, they are grown in culture using the same conditions. Briefly, ECs are seeded onto gelatin-coated dishes and propagated using modified Iscove's growth medium supplemented with 8% FCS, 2% prepartum maternal serum, $5\times10^{-4}$ M dibutyryl cAMP, $3.3\times10^{-5}$ M isobutylmethylxanthine, $1\times10^{-4}$ M hypoxanthine, and 1.5× 10.4 M thymidine, as described. Lipton, B. H. et al., *Exp. Cell Res.* 199:279–291 (1992). ECs grown under these conditions maintain an epithelioid configuration and can be passaged 3–5 times upon confluence using 0.05% trypsin, 0.01% EDTA.

Cell Culture. KS tumor cell lines are selected from existing frozen stocks, as well as from newly enrolled HIV-1 positive individuals with KS lesions who are otherwise healthy. KS cells are grown using routine protocol and growth medium. New KS cell lines are established as AIDS patients with KS present and take punch biopsies of their skin lesions for tissue culture. KS growth medium consists of RPMI 1640 with 15% FBS, nutrodoma-Hu (5%) and conditioned medium from the HTLV-II infected T lymphocyte line 38-10. Four different KS tumor lines, two from the skin (KS-I, KS-II, the ocular conjunctive (KS-III) and pleural effusion (KS-IV)) are currently available from co-inventor Dr. Brian J. Nickoloff, University of Michigan, Ann Arbor, Mich. A line of EC, SVEC4-10, isolated from C3H/HeJ peripheral lymph node and immortalized by transient infection with SV40 strain A, provided by Dr. Kathryn O'Connell, John Hopkins University, are used for tumorigenesis studies in nude mice. O'Connell, K. A., et al. *J. Immunol.* 144:521–525 (1990); O'Connell, K. A. et al., *J. Inves. Derm.* 100:742–745 (1993) and O'Connell, K. A. et al., *Am. J. Pathol.* 139:743–749 (1991). These cells display many features in common with KS tumor cells. Cells are maintained in DME medium with 10% FBS and are passaged weekly. The tumorigenic potential of EC transduced with HIV tat, HPV E61E7, and SV40 large T antigen is also assessed. The transformation frequency with newly generated lines is also assessed by calculating the number of "transformed foci" that arise in surface culture following transfection.

Detection of SF. SF activity in conditioned medium is quantitated using the MDCK scatter assay as described. Rosen, E. M. et al., *Cancer Invest.* 8:647–650 (1990). Briefly, samples are serially diluted in DMEM and incubated with one day old colonies of MDCK cells for 20 hr in 96-well plates. Cells are stained and examined for Scattering (colony spreading and cell separation). SF ELISA detects immunoreactive protein using a double antibody sandwich technique as described in Grant, D. S. et al., *PNAS* (USA) 990:1937–1941 (1993). This assay is specific for SF, and the lower limit of detection is 0.1 ng/100 µl. Northern blot and PCR analysis for SF mRNA is performed using standard procedures, and a cDNA probe as well as specific primer sequences, that are verified to react with only SF mRNA.

Transdifferentiation Experiments. HUVECs and MVECs are transdifferentiated in an identical fashion. These ECs are grown to sub-confluence in conventional medium and then exposed to SF or cytokines of interest either singly or in combination for 24–48 hrs. Highly purified SF is provided, as previously described. The SF final concentration is 250 units/ml; IL-1β-final concentration 50 units/ml, and histamine hydrochloride (purchased from Sigma Chemical Corp., St. Louis, Mo.) used at $5\times10^{-5}$ M. ECs are visualized by phase contrast microscopy to monitor morphological changes, indicative of transdifferentiation.

Transfection. The HIV-tat gene ((pHIV-LTR-tat 3), HPV 16 E6/E7) which have been previously cloned are ligated with pcDNA/NEO, and transfected into 4 different existing KS tumor cell lines, EC isolated from the dermis of normal volunteers and AIDS patients, and the continuous line of BCE by either electroporation or lipofection. These constructs have been successfully transfected into human keratinocyte cell line (HACAT) using this approach. This approach has also been successful for human mammary carcinoma cell lines. Transfected KS cell lines are selected in medium containing G418 (Neomycin: 200 µg/ml) subcloned, and tat expression, E6/E7, and SV40 large T antigen are determined. The pCMVβ expression vector from Clonetech is used to introduce β-galactosides into EC.

PCR Analysis. The cytokines of interest which are detected include: IL-1β, IL-6, IL-8, IL-10, GM-CSF, TGF-α, TGF-β, ICAM IFN-γ, with β-actin serving as the housekeeping gene. PCR amplification is performed as described above. Briefly total RNA is isolated by acid guanidinium isothiocyanate-phenol-chloroform extraction. The mRNAs in the extract are reversed transcribed into cDNAs with oligo d(T) as primer, in the presence of 0.2 mM dNTPs and MoMuLV reverse transcriptase (Gibco-BRL). Equal amounts of cDNA are subjected to 35 cycles of PCR amplification. The reaction mixture contains 2.5µ tac polymerase, 2.5 mM $MgCl_2$ 0.15 mM dNTPs (Perkin-Elmer Cetus) and 20 pM each of 5' and 3' primers. Each cycle consists of denaturation at 94° C. for 1 min, followed by 1 min of annealing and extension at 62° C. for factor XIIa (outer primers), and 65° C. for factor XIIIa (internal primers) and β-actin. PCR reactions are subjected to one cycle of denaturation at 94° C. for 3 min before the first cycle and one cycle of annealing/extension at 72° C. for 7 min at the end. All reactions are subjected to the hot-start PCR method, as described in Chou, Q. M. et al., *Nucleic Acids* 20:1717–1722 (1992). The PCR products are extracted with chloroform, precipitated and analyzed on a 3% agarose gel, stained with ethidium bromide, and visualized under UV illumination. The validity of the amplified product is insured using nested PCR primers specific for factor XIIIa mRNA and by including control reactions lacking various reagents and cDNA. These experiments are performed separately for each EC isolate and EC lines as described above. β-actin was utilized as a control for loading. The Genebank base pair (bp) sequence numbers (5'-3') for the PCR primers used are: factor XIIIa internal primers, 1999–2020 and 2244–2224; β-actin primers, 1259–1278 and 2374–2351. The expected sizes of the amplified sequences are 245 bp for factor XIIIa and 531 bp for β-actin. Using this same protocol, PCR amplification of the following cytokine mRNAs is performed. The Genebank bp sequence numbers (5'-3') for the PCR primers are: interleukin 1β (IL-1β), 393–412 and 639–628: IL-6, 148–167 and 342–321: IL-8, 75–95 and 375–343; intercellular adhesion molecule-1 (ICAM-1), 1246–1466 and 1594–1586; IL-10, 313–339 and 665–639: GM-CSF, 36–56 and 472–449; TGF-α, 35–58 and 522–495; TGF-β, 1678–1697 and 2006–1994.

In Situ Hybridization and Immunohistochemistry. Skin from tat mice and nude mice bearing transplanted EC tumors is processed for in situ hybridization initially using a modification of the method of Angerer, L. M. et al. *Meth. Enzymol.* 152:649 (1987) and for immunohistochemistry using the avidin-biotin complex method Angerer, L. M. et al. *Meth. Enzymol.* 152:649 (1987). Animals are killed by cervical dislocation, wounds are removed, and immersed in 4% paraformaldehyde in 0.9% NaCl; 50 mM sodium phosphate pH 7.4 for 1–3 hrs at 0° C. Tissues are washed twice in 0.5M PBS pH 7.4 for 30 min at 0° C., dehydrated through increasing grades of alcohol, incubated in 2 changes of xylene for 30 min each, and embedded in paraffin. Five μm sections are cut on a rotary microtome and placed on Chromerge-cleaned Vectabond (Vector Labs) coated slides. Alternatively 7 μg frozen sections is prepared from freshly isolated tissue that is snap frozen in hexane on acetone-dry ice. Prehybridization treatments consist of treating deparaffinized sections with proteinase K (1 μg proteinase K/ml in 100 mM Tris-HCL, 50 mM EDTA, pH 8.0 at 37° C.) for 30 min followed by treatment with acetic anhydride to reduce electrostatic binding of probe. DNA is denatured after proteinase K and acetic anhydride treatments by immersing slides in 95% formamide, 0.1×SSC (150 mM NaCl, 15 mM Na citrate, pH 7) for 15 min at 65° C. and transferred to cold 0.1×SSC for 5 min. Sections are prehybridized in hybridization buffer without probe overnight at 37° C. The hybridization mix consists of 50% formamide, 1×Denhardt's solution, 1 mg yeast tRNA/ml, salmon sperm DNA 100 μg/ml, 3×SSC, 100 mM DTT, and 10% dextran sulfate. Sections are incubated in hybridization buffer with probe for 24 hr at 37° C. After hybridization, the slides are washed twice for 10 min in 2×SSC followed by treatment for 30 min at 22° C. with 20 μg/ml RNase A, washing 2× for 10 min in 2×SSC, for 2 hr in 0.2×SSC at 42° C. and finally 2× for 10 min each in 0.5×SSC at 22° C. All post hybridization washes except for the final washes in 0.5×SSC contain 10 mM β-mercaptoethanol and 1 mM EDTA. After hybridization and washing, slides are dehydrated through graded alcohols containing 0.3M NH$_4$AC, dried under vacuum, and then coated with Kodak NTB type 2 emulsion diluted 1:1 with distilled water. Autoradiographs are exposed for 2–3 weeks with desiccant at 4° C. in the dark. Slides are developed in Kodak D19 developer (1:1 dilution), fixed in Kodak Ectaflow fixer and stained with hematoxylin and eosin. Contiguous sections are used for immunohistochemistry and immunoperoxidase stained with polyclonal antibodies to the various cytokines and adhesion molecules. Briefly, slides are incubated with primary antibodies which have been biotinylated, followed by incubation with Vectastain ABC immunoperoxidase complexes (Vector Laboratories, Burlingame, Calif.). Slides are developed with 3'3'-diaminobenzidine as the substrate and then counterstained with Gill's Hematoxylin.

Probes

A) DNA probes. DNA probes are used for all RNA and Southern blot analysis (Northern blots), (pHu SF (human SF cDNA) and pHu c-met (human cDNA)). Inserts are excised from the plasmid by appropriate restriction enzyme digestion and isolated by agarose gel electrophoresis and electroelution of the probe fragment. Labelling of probes with $^{32}$p dATP is performed by the random oligomer priming method of Feinberg and Volgestein (Feinberg, A. P. et al., *Anal Biochem.* 132:6 (1983)) utilizing the Random Primers DNA Labelling System from BRL Life Technologies (Gaithersburg, Md.). Probes are routinely labelled to a specific activity of greater than $10^8$ cpm/μg with this system. If necessary, free nucleotide is removed from labelled probes by spin column chromatography.

B) RNA probes. Anti-sense RNA probes for in situ hybridization procedures are prepared utilizing the Riboprobe System (Promega, Madison, Wis.). In this system, the cloning vectors bear a polylinker flanked by SP6 and T RNA polymerase promoters. Depending upon the orientation of the insert, RNA probes incorporating $^{35}$S labelled NTPs are transcribed from either SP6 or T7 RNA polymerase promoter in the anti-sense direction. Sense orientation probes serve as a negative control in in situ experiments.

In Vivo and In Vitro Bioassays of Angiogenesis

A) Cornea/Neovascularization. Angiogenic activity is assayed in the avascular cornea of F344 female rat eyes (Harlan Labs, Madison, Wis.) as previously described. Polverini, P. J. et al., *Lab Invest.* 51:635–642 (1984) and Gimbrone Jr., M. A. et al., *J. Natl. Cancer Inst.* 52:413–427 (1974). Concentrated CM (~5 μg of protein) is combined with an equal volume of sterile HYDRON® casting solution (interferon Sciences, New Brunswick, N.J.) and 10 μl aliquot is pipetted onto the surface of 1 mm diameter TEFLON® rods (DuPont Corporation) glued to the surface of a glass petri dish. Pellets are air dried in a laminar flow hood for 1 hr and placed within a surgically crated intracorneal pocket ~1.5 mm from the limbus. Corneas are observed every other day up to day 7 when animals are perfused sequentially with lactated ringers solution and colloidal carbon. Responses are scored as positive when sustained directional ingrowth of capillary sprouts and hairpin loops toward the implant is detected. Negative responses are recorded when no growth is detected or when only an occasional sprout or hairpin loop showing no evidence of sustained growth is observed.

B) Endothelial Cell Migration. Endothelial cell chemotaxis is performed in a 48-well, blind well chemotaxis chambers (Nucleopore Corp., MD) as previously described. Ratinejad, F., *Cell* 56:345–355 (1989) and Good, D. J., *PNAS* (USA) 87:6624–6628 (1990). Nucleopore chemotaxis membranes (5 μm pore size) are prepared by soaking them sequentially in 3% acetic acid overnight and for 2 hr in 0.1 mg/ml gelatin. Membranes are rinsed in sterile water, dried under sterile air, and stored at room temperature for up to 1 month. Bovine adrenal gland capillary endothelial cells (BCE), maintained in gelatin-coated flasks in DME with 10% FBS are used as target cells. Twenty four hours before use BCE are starved in DME with 0.1% BSA. Twenty five microliters of cells, suspended at a concentration of $1 \times 10^6$ in DME with 0.1% BSA are dispensed into each of the bottom wells. A chemotaxis membrane is positioned atop the bottom wells, chambers are sealed, inverted and incubated for 2 hr. to allow cells to adhere to the membrane. Chambers are then reinverted, 50 μl test media is dispensed into the top wells and reincubated for an additional 2 hr. Membranes are fixed and stained with Diff-Quick staining kit (American Scientific Products) to enumerate membrane bound cells and cells which had migrated through the membrane to the opposite surface were counted. Four replicates, 10 fields per replicate, are tested for each sample, and experiments are repeated at least twice. Results are expressed as the total number of endothelial cells that migrated across the filter in 10 high powered (×400) fields. Statistical comparisons between control and experimental grow ups are made using Student's t test.

C) Preparation of RNA. Total cellular RNA is prepared from either tissues or cultured cells by the guanidine isothiocyanate lysis and cesium chloride gradient centrifugation. Davis, L. G. et al., *Basic Meth. Mol. Biol.* Elsevier, N.Y. (1986) and Sambrook, J. et al., "Molecular Cloning: A Laboratory Manual" 2nd ed. Cold Springs Harbor Laboratory, NY, pp 931–957 (1989). All solutions and plasticware is treated with diethyl-pyrocarbonate to eliminate RNase activity. Approximately $5 \times 10^7$ cultured cells are lysed in 3.5 ml of lysis solution containing 4M guandine isothiocyanate, 25 mM Na Acetate, and 120 mM β-mercaptoethanol. Lysates are layered onto 2 mls of a CsCl solution (5.7 M CsCl in 25 mM Na Acetate) and the gradient is subjected to configuration in a Beckman SW50.1 rotor at 35,000 rpm for 18 hr. The RNA pellet is resuspended in 200 µl of 0.3M Na Acetate and extracted with phenol, phenol-chloroform and chloroform. Quantitation of RNA is performed spectrophotometrically. Aliquots of RNA are stored as ethanol precipitates at −70° C.

D) Northern and Southern analysis. Northern and Southern analysis is performed utilizing Gene Screen Plus Hybridization Transfer Membrane (DuPont NEN, Boston, Mass.) according to the manufacturer's directions. For Northern analysis, 10 to 25 µg of total RNA per lane is separated by standard formaldehyde gel electrophoresis and blotted onto Gene Screen Plus utilizing 10×SSC (standard saline citrate solution, 1×: 0.15M NaCl, 0.15M NaCitrate). Blots are baked at 80° C. for 2 hr for formaldehyde reversal. Prehybrdization and hybridization is performed at 60° C. under aqueous conditions in hybridization buffer containing 1% SDS, 1M NaCl, 10% dextran sulfate and 100 µg/ml sheared and boiled salmon sperm DNA. For hybridization, probes are denatured by boiling, quick-chilled on ice and added to the hybridization solution at a final concentration of 1–4× $10^6$ cpm/ml. Washes are performed at 60° C. in 2×SSc, 1% SDS. If necessary, a final wash at room temperature is performed in 0.1×SSC. Blots are subjected to autoradiography on Kodak X-O-Mat AR film with Cronex Lightening Plus Intensifying Screens at −70° C. For Southern analysis, DNA is subjected to restriction enzyme digestion and standard agarose gel electrophoresis. Prior to blotting, gels are incubated in 0.4N NaOH-0.6M NaCl for 30 min at room temperature and then neutralized in 1.5M NaCl-.5M Tris-HCl, pH 7.5 for 30 min at room temperature. Blotting, hybridization and autoradiography is performed as described for Northern analysis.

E) Western Blot Analysis. Western analysis is conducted as previously described. Good, D. J., *PNAS* (USA) 87:6624–6628 (1990). Briefly polyacrylamide gels are equilibrated for 30 min in transfer buffer (20 mM Tris, 150 mM glycine [pH8.3]) and transferred to GeneScreen membranes for 1 hr at 100V in a Mini Transblot apparatus (BioRad). After 30 min in blocking solution (PBS with 1% non-fat dry Carnation milk), membranes are incubated at room temperature for 1 hr with primary antiserum to gp140 and to the various growth/angiogenic factors at an appropriate dilution in blocking solution, washed 3× with PBS, and incubated in horseradish peroxidase conjugated anti IgG for 1 hr at room temperature or overnight at 4° C. The enzyme reaction is developed with substrate solution containing 500 µg/ml diaminobenzidine, 0.02% cobalt chloride, and 0.03% hydrogen peroxide. To adsorb antigenically cross-reacting material out of CM for immunoprecipitations, fixed staphylococci are washed in PBS and rocked for 1 hr at 4° C. with 100 µl of CM from Mø and centrifuged, and the supernatant is tested in the cornea.

HIV tat Mice and Tumor Transplantation Studies. CD1 mice that have been screened for an intact LTR-tat3 sequence, are provided by Gilbert Jay. Confirmation of expression of this sequence in the skin and KS-like tumors that spontaneously arise in $F_1$ offspring is performed by Northern blot analysis. Pathogen free CD1 (outbred) nu/nu male mice serve as recipients of the transplantable SVEC4-10 line, KS tumors and lines and all control ECs. One to six million cells in 0.2 ml of buffered saline are injected subcutaneously and injection sites are examined for the development of tumors. Tumor size is recorded and volume is calculated as a measure of growth over time. In addition, tumors are excised and phenotyped according to KS protocol. All cells injected are phenotyped before and after implantation.

SPECIFIC EXAMPLE 3

As set forth above, although it is not the intent herein to be bound by any particular theory, a model for generally understanding the pathophysiology of KS lesions in AIDS patients and in particular the role of SF, has been postulated. This multi-step schema portrays how a vicious cycle can be established within a KS lesion for continued production of HIV-1, SF, and dysfunctional T lymphocytes.

KS lesion formation begins when a T cell becomes infected by HIV-1 and is induced to produce SF. This locally produced SF can the induce vascular lining cells to migrate into a perivascular position and acquire a transdifferentiated phenotype. An immortalization step is suggested (transformation), because in vitro when ECs were transdifferentiated by SF, they cannot continue to divide beyond more than 2–3 additional passages before they become terminally senescent. KS tumor cells in vivo on the other hand, can be maintained for several dozen passages. SF is then portrayed as providing an important mitogenic signal to expand the size of the lesion not only by increasing the number of KS tumor cells, but also by promoting an angiogenic tissue response to support lesion expansion. As the lesion begins to expand, an early non-specific inflammatory reaction occurs producing IFN-γ which induces HLA-DR, ICAM-1, but not B7 on the KS tumor cells. As T cells accumulate and bind to these cytokine activated KS tumor cells, they are rendered dysfunctional, and cannot properly combat the expanding lesion with escape from immune surveillance. During tumor formation, dermal dendrocytes continue to accumulate to provide accessory cell function to the T cells, but rather than necessarily improving the immunological response, they end up becoming participants in productive infection of HIV-1, leading to further T cell related abnormalities.

These proposed phenomena are all consistent with the typical histological changes observed in vivo for KS lesions, as well as the immunophenotypic, and functional immunological results obtained in vitro for ECs, KS tumor cells, dendritic cells, and T lymphocytes. As can be understood from the above model, a positive feedback loop would exist once the process of SF production is initiated, because local release of HIV-1 could further enhance SF production by T lymphocytes.

As mentioned above, it is believed that B7 is not induced on KS tumor cells. In particular, a study has been performed to determine whether IFN-γ could induce B7 expression on KS tumor cells. A description of the study and results are set forth below.

Two KS lines were tested at least three times using an IFN-F concentration that induces B7 on monocytes and ECs. In all tests, no B7 was expressed by either KS line, despite induction of HLA-DR, and increased expression of ICAM-1 compared to non-IFN-γ treated KS cells. Two different reagents were used to measure B7 expression, a mouse anti-human B7 (IgG1) antibody prepared by Repligen Corp. (Boston, Mass.) and an even more sensitive reagent, the human chimera fusion protein CTLA4-Ig, kindly provided by Peter Linsley (Seattle, Wash.). This fusion protein binds B7 with a Kd of 12 nM, approximately 20-fold greater than the avidity of the interaction between B7 and a CD28 Ig fusion protein. The specificity of both the Repligen anti-B7 mAB, and CTLA4-1g was confirmed by using CHO cells either mock transfected or B7-transfected, as well as by immunoprecipitation of $^{125}$I labeled cell lines expressing B7 mRNA. Such a cell line is M16B cells that has successfully detected all 4 mRNA transcripts for B7 (Savage, C. O. et al.,

*Cell Immunol.* 137:150–159 (1991)). Immunostaining 5 different KS cells revealed focal B7 expression epidermal Langerhans cells, ECs, and dermal dendrocytes, but not KS tumor cells. Using these reagents, it was observed that unlike cultured ECs that upregulate B7 expression following IFN-γ (500 U/ml, 48 hrs), as well as ICAM-1 and HLA-DR, KS tumor cells only express ICAM-1 and HLA-DR, but not B7.

A study was then performed to determine whether untreated or IFN-γ-treated KS cells could stimulate peripheral blood T cells in three different assays including: 1) 7-day allogeneic MLR; 2) 3-day PHA mediated accessory cell role; and 3) 4-day superantigen presentation. While IFN-γ-treated ECs stimulated T cells in all three assays, the two KS cell lines tested did not support significant T cell proliferation in any of the assays. Representative $^3$H-thymidine incorporation results for the superantigen (i.e. SEB-10 μg/ml) mediated reaction are shown in Table 2 below, to illustrate the typical positive response by T cells to IFN-γ-treated ECs, but not IFN-γ-treated KS cells. $5\times10^4$ highly purified T cells were combined with $5\times10^3$ irradiated (3000 R) stimulator cells in 200 μl RPMI+10% FCS. Since these were allogenic combinations, IFN-γ-treated ECs provided both an allo-response, plus an added response with SEB, in line with a previous report (Damle, N. K. et al., *J. Immunol.* 150:726–735 (1993)). It should also be noted that if even increasing the number of IFN-γ-treated KS cells to $25\times10^3$/well, did not induce proliferation. Thus, it appears that KS tumor cells cannot be induced to express B7 by IFN-γ, and they fail to provide necessary accessory signals for T cell activation/proliferation.

TABLE 2

| Cell Combinations | Day 3 CPM* | Cell Combinations | Day 3 CPM* |
|---|---|---|---|
| PBMC + medium alone | 2,005 | T cells + ECs | 485 |
| PBMC + SEB | 23,992 | T cells + IFN-γ treated ECs | 16,911 |
| T cells alone | 264 | T cells + ECs + SEB | 3,965 |
| T cells + SEB | 325 | T cells + IFN-γ treated ECs + SEB | 59,516 |
| ECs alone | 295 | T cells + KS cells | 450 |
| IFN-γ treated ECs alone | 304 | T cells + IFN-γ treated KS cells | 512 |
| KS cells alone | 426 | T cells + KS cells + SEB | 448 |
| IFN-γ treated KS cells alone | 425 | T cells + IFN-γ treated KS cells + SEB | 834 |

*Mean values of triplicate wells are presented (SEM < 15%).

These in vitro results suggest that KS tumors may actually be tissue sites at which T cells may be down-modulated or rendered anergic should they interact with the HLA-DR and ICAM-1 positive, but BB-1/B7 negative KS tumor cell. While several groups have postulated various mechanisms by which T cell dysfunction may arise in HIV-1 infected individuals, that involve anergy, apoptosis, or preferential induction of a TH2 type response (Meyaard, L. et al., *Immunol. Tod.* 14:161–167 (1993); Sheppard, H. W. et al., *Immunol. Tod.* 12:423 (1991); Clerici, M. et al., *Immunol. Tod.* 14:107–111 (1993); Weiss, R. A., *Science* 260:1273–1279 (1993) and Pantaleo, G. et al., *N. Eng. J. Med.* 328:327–335 (1993)), the potential contribution of cytokine activated KS tumor cells is a novel proposition. By either gene transfer or a cytokine that can induce B7, it is possible that such induction on the KS tumor cell will serve as a therapeutic strategy for immune intervention in KS.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All publications cited herein are specifically incorporated by reference.

We claim:

1. A method of inhibiting Kaposi's sarcoma tumor cell growth in a patient comprising inhibiting the effect of scatter factor.

2. The method of claim 1, further comprising the step of administering to the patient a therapeutically effective amount of an antibody to scatter factor, in a biologically compatible form.

3. The method of claim 1, further comprising the step of blocking the c-met receptor.

4. The method of claim 2, further comprising the step of administering to the patient a therapeutically effective amount of an antibody selected from the group consisting of antibody to oncostatin M, antibody to IL-6, and combinations thereof, in a biologically compatible form.

5. The method of claim 3, wherein blocking the c-met receptor further comprises the step of administering to the patient a therapeutically effective amount of an antibody to c-met, in a biologically compatible form.

6. The method of claim 3, wherein blocking the c-met receptor further comprises the step of administering to the patient a therapeutically effective amount of a non-stimulatory ligand capable of binding but not stimulating the c-met receptor, in a biologically compatible form.

7. The method of claim 3, further comprising the step of administering to the patient a therapeutically effective amount of an antibody selected from the group consisting of antibody to oncostatin M, antibody to IL-6, and combinations thereof, in a biologically compatible form.

8. A method of treating a patient having Kaposi's sarcoma by inhibiting Kaposi's sarcoma tumor cell growth, comprising the step of inhibiting the effect of scatter factor.

9. The method of claim 8, wherein the step of inhibiting further comprises administering to the patient a therapeutically effective amount of an antibody to scatter factor, in a biologically compatible form.

10. The method of claim 8, wherein the step of inhibiting further comprises blocking the c-met receptor.

11. The method of claim 9, further comprising the step of administering to the patient a therapeutically effective amount of an antibody selected from the group consisting of antibody to oncostatin M, antibody to IL-6, and combinations thereof, in a biologically compatible form.

12. The method of claim 10, wherein blocking the c-met receptor further comprises the step of administering to the patient a therapeutically effective amount of an antibody to c-met, in a biologically compatible form.

13. The method of claim 10, wherein blocking the c-met receptor further comprises the step of administering to the patient a therapeutically effective amount of a non-stimulatory ligand capable of binding but not stimulating the c-met receptor, in a biologically compatible form.

14. The method of claim 10, further comprising the step of administering to the patient a therapeutically effective amount of an antibody selected from the group consisting of antibody to oncostatin M, antibody to IL-6, and combinations thereof, in a biologically compatible form.

15. A method of inhibiting Kaposi's sarcoma tumor cell growth in a patient comprising the steps of:

a) administering to the patient a therapeutically effective amount of an antibody to scatter factor, in a biologically compatible form; and b) administering to the patient a therapeutically effective amount of an antibody to c-met, in a biologically compatible form.

16. The method of claim 15, further comprising the step of:

c) administering to the patient a therapeutically effective amount of an antibody selected from the group consisting of antibody to oncostatin M, antibody to IL-6, and combinations thereof, in a biologically compatible form.

17. A method of inhibiting angiogenic activity in Kaposi's sarcoma comprising inhibiting the effect of scatter factor.

18. The method of claim 17, further comprising the step of administering to the patient a therapeutically effective amount of an antibody to scatter factor, in a biologically compatible form.

* * * * *